US006436962B1

(12) United States Patent
Hoffman et al.

(10) Patent No.: US 6,436,962 B1
(45) Date of Patent: Aug. 20, 2002

(54) ARYLHYDANTOIN DERIVATIVES AND USES THEREOF

(75) Inventors: Jacob M. Hoffman, Lansdale; Mark G. Bock, Hatfield; Robert M. DiPardo; Linda S. Payne, both of Lansdale; Michael A. Patane, Harleysville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/671,518

(22) Filed: Sep. 27, 2000

Related U.S. Application Data

(60) Provisional application No. 60/156,753, filed on Sep. 30, 1999.

(51) Int. Cl.$^7$ .................... A61K 31/445; C07D 401/00; C07D 233/02; C07D 233/72
(52) U.S. Cl. .................... 514/331; 514/341; 514/344; 546/210; 546/215; 546/229; 548/311.1; 548/317.1
(58) Field of Search .................. 514/331, 341, 514/344; 546/210, 215, 229; 548/311.1, 317.1

(56) References Cited

U.S. PATENT DOCUMENTS

| | | | |
|---|---|---|---|
| 3,892,748 A | 7/1975 | Hayao et al. | 260/268 |
| 3,994,904 A | 11/1976 | Havera et al. | 260/293.7 |
| 4,006,232 A | 2/1977 | Hayao et al. | 424/250 |
| 4,061,760 A | 12/1977 | Havera et al. | 424/267 |
| 4,110,536 A | 8/1978 | Havera et al. | 544/139 |
| 4,675,403 A | 6/1987 | Abou-Gharbia et al. | 544/230 |
| 5,731,331 A | 3/1998 | Merce-Vidal et al. | 514/341 |

FOREIGN PATENT DOCUMENTS

| | | |
|---|---|---|
| DE | 2434951 | * 2/1975 |
| EP | 0 204 597 | 5/1986 |
| EP | 0 748 800 | 12/1996 |
| WO | WO 92/00073 | 1/1992 |
| WO | WO 92/16213 | 10/1992 |
| WO | WO 94/08040 | 4/1994 |
| WO | WO 94/10989 | 5/1994 |
| WO | WO 94/22829 | 10/1994 |
| WO | WO 96/14846 | 5/1996 |
| WO | WO 96/40135 | 12/1996 |
| WO | WO 97/17969 | 5/1997 |
| WO | WO 97/42956 | 11/1997 |
| WO | WO 98/57632 | 12/1998 |
| WO | 9857632 | * 12/1998 |
| WO | WO 98/57638 | 12/1998 |
| WO | WO 98/57639 | 12/1998 |
| WO | WO 98/57640 | 12/1998 |
| WO | WO 98/57641 | 12/1998 |
| WO | WO 98/57642 | 12/1998 |
| WO | WO 98/57940 | 12/1998 |

OTHER PUBLICATIONS

R. Hudkins et. al., "Phenytoin Derivatives as Potent o Ligands", Bioorganic & Medicinal Chemistry Letters, vol. 4 No. 18 pp. 2185–2188 (1994).
A. Ramu et al., "Reversal of multidrug resistance by phenothiazines and structurally related compounds", Cancer Chemother Pharmacol, vol. 30: pp. 165–173 (1992).
C. Valenzuela et al., "Electrophysiologic Interactions Between Mexiletine–Quinidine and Mexiletine–Ropitoin in Guinea Pig Papillary Muscle", Journal of Cardiovascular Pharmacology vol. 14: pp. 783–789 (1989).
E. Hong et al., "Antiarrhythmic Activity of Ropitoin in Rats Subjected to Coronary Artery Ligation", Proc. 'West. / Pharmacol. Soc. vol. 29, pp. 15–17 (1986).
H. Vidrio et al., "Antiarrhythmic activity of TR 2985, a Novel Diphenylhydantoin Derivative", Drug. Res. vol. 30(I), pp. 12–17 (1980).
J. Lynch et al., "Antiarrhythmic vs. Antifibrillatory Activity of the Basic Diphenylhydantoin Derivative 3–[3–(4–Phenyl–l–piperidyl)propyl] –5–(4–methoxyphenyl)–5–phenylhydantoin Hydrochloride"Drug Res. 36(I), Nr. 3 pp. 475–481 (1986).
A. Elizalde et al., "Effects of the novel antiarrhythmic compound TR 2985 (ropitoin) on action potentials of different mammalian cardiac tissues", Naunyn–Schmiedeberg's Arch Pharmacol, vol. 337, pp. 316–322 (1988).
E. Ware, "The Chemistry of the Hydantoins", Chem Rev. vol. 46, pp. 403–457 (1950).
Michel, et al., Naunyn–Schmiedeberg's Arch. Pharmacol. vol. 352, pp. 1–10 (1995).

* cited by examiner

Primary Examiner—Mukund J. Shah
Assistant Examiner—Sudhaker B. Patel
(74) Attorney, Agent, or Firm—Baerbel R. Brown; Kenneth R. Walton; Catherine D. Fitch

(57) ABSTRACT

Arylhydantoin derivatives and their pharmaceutically acceptable salts are disclosed. The synthesis of these compounds and their use as alpha 1a adrenergic receptor antagonists is also described. One application of these compounds is in the treatment of benign prostatic hyperplasia. These compounds are typically selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

31 Claims, No Drawings

ARYLHYDANTOIN DERIVATIVES AND USES THEREOF

This application claims the benefit of U.S. Provisional Application No. 60/156,753 filed Sep. 30, 1999, the disclosure of which is hereby incorporated by reference in its entirety.

FIELD OF THE INVENTION

The present invention relates to arylhydantoin derivatives and pharmaceutically acceptable salts thereof, their synthesis, and their use as alpha 1a adrenoceptor antagonists. The arylhydantoin derivatives of the present invention include, but are not limited to, compounds having (1-azacycloalkyl)alkyl, ((4-amino)-1-azacycloalkyl)alkyl, or (spiroazacycloalkyl)alkyl groups as side chains on a hydantoin ring nitrogen. The compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, β1, and β2 subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (Progress in Basic and Clinical Pharmacology series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352: 1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype as reported. In addition, in WO 92/16213, combinations of 5α reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor have made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists. Yet another example is EP 748800, which discloses, inter alia, certain arylpiperazinylpropyl substituted pyrimidinediones useful as alpha 1 adrenoceptor antagonists. Still other alpha 1a selective antagonist compounds are disclosed in WO 98/57632, WO 98/57638, WO 98/57639, WO 98/57640, WO 98/57641, WO 98/57642, and WO 98/57940.

U.S. Pat. No. 3,994,904 discloses 3-substituted 5-phenyl-5-pyridyl-hydantoins in which the C-3 carbon is attached by $C_1-C_3$ alkylene to 4-phenyl-1-piperidinyl, 4-phenyl-4-hydroxy-1-piperdinyl, or 4-phenyl-4-($C_1-C_3$ alkoxy)-1-piperidinyl. U.S. Pat. No. 4,006,232 discloses certain 3-substituted-5,5-diphenylhydantoin derivatives in which the C-3 carbon of the hydantoin ring is attached by a lower alkylene bridge to, inter alia, 4-phenyl-1-piperidinyl, 4-hydroxy-4-phenyl-1-piperidinyl, or 4-phenyl-1-piperazinyl. U.S. Pat. No. 4,110,536 discloses 3-substituted 5-(indol-3-yl)hydantoin derivatives, in which the C-3 carbon is attached by $C_1-C_3$ alkylene or 2-hydroxytrimethylene to, inter alia, 4-phenylpiperidin-1-yl or 4-hydroxy-4-phenyl-piperidin-1-yl. In all three of the foregoing patents, the compounds are disclosed to be useful for treating cardiac arrhythmias.

3-[3-(4-phenyl-1-piperdinyl)propyl]-5-(4-methoxyphenyl)-5-phenylhydantoin (also known as ropitoin) has been disclosed to be useful as an antiarrhythmic drug. See, for example, Vidrio et al., *Arzneim.-Forsch/Drug Res.* 1980, 30(I): 12–17; Lynch et al., *Arzneim.-Forsch./Drug Res.* 1986, 36(I): 475–481; Elizalde et al., *Naunyn-Schmiedeberg's Arch Pharmacol.* 1988, 337: 316–322; Valenzuela et al., *J. Cardiovascular Pharm.* 1989, 14: 783–789; and Hong et al., *Proc. West. Phannacol Soc.* 1996, 29: 15–17.

U.S. Pat. No. 4,675,403 discloses 3-aminoalkyl derivatives of 5,5-disubstituted hydantoins having psychotropic acitivity, including certain 3-(4-hydroxy-4-phenylpiperdin-1-yl)alkyl derivatives and certain 3-(4-substituted piperazin-1-yl)alkyl derivatives. Hudkins et al., *Bioogranic & Medicinal Chem. Lett.* 1994, 4: 2185–2188, discloses the preparation of a series of 4-phenylpiperidinyl and 4-phenylpiperazinyl alkyl spaced 5,5-diphenylhydantoins and evaluates the potency of the compounds as sigma ligands, The instant patent specification discloses novel arylhydantoin derivatives which bind to the human alpha 1a receptor. These compounds are further tested for binding to other human alpha 1 receptor subtypes, as well as counter-screened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides arylhydantoin derivatives and pharmaceutically acceptable salts thereof for the treatment of urinary obstruction caused by benign prostatic hyperplasia (BPH). The compounds antagonize the human alpha 1a adrenergic receptor at nanomolar and subnanomolar concentrations, while exhibiting lower affinity for the alpha 1d and alpha 1b human adrenergic receptors and many other G-protein coupled receptors. This invention can have the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

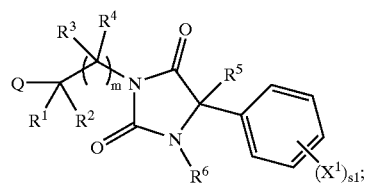

wherein Q is

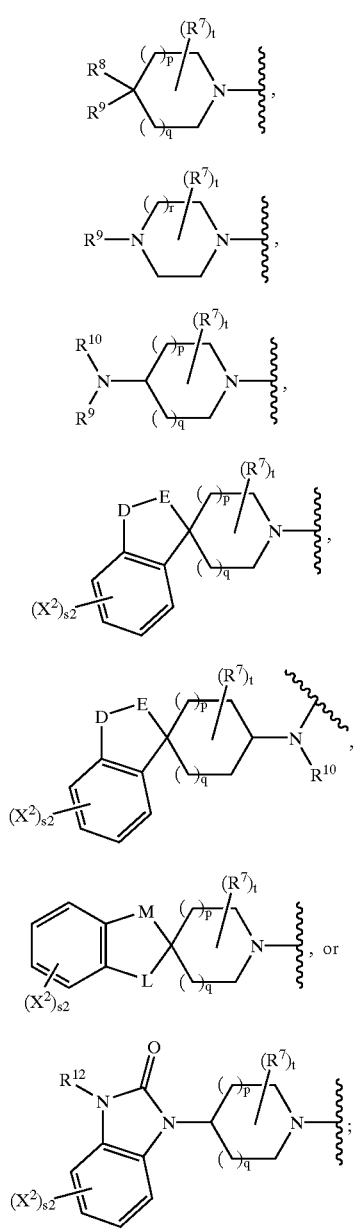

$R^1$, $R^2$, $R^3$ and $R^4$ are each independently selected from hydrogen, fluorine, $C_1$–$C_6$ alkyl, and $C_3$–$C_8$ cycloalkyl;

$R^5$ is $C_1$–$C_6$ alkyl, phenyl, substituted phenyl, naphthyl, substituted naphthyl, heterocyclic, or substituted heterocyclic; wherein each of the substituents on substituted phenyl or substituted naphthyl is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $C_2$–$C_8$ alkoxyalkyl, or fluorinated $C_2$–$C_8$ alkoxyalkyl; and wherein each of the substituents on substituted heterocyclic is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $C_2$–$C_8$ alkoxyalkyl, fluorinated $C_2$–$C_8$ alkoxyalkyl, or phenyl;

$R^6$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $(CH_2)_{1-4}CO_2R^d$, $(CH_2)_{1-4}C(=O)N(R^d)_2$, $C_2$–$C_8$ alkoxyalkyl, or fluorinated $C_2$–$C_8$ alkoxyalkyl;

each $R^7$ is a substituent connected to a ring atom other than $C(R^8R^9)$, spiro substituted carbon, or N and is independently hydrogen, $C_1$–$C_4$ alkyl, or $(CH_2)0$-$2CO_2R^d$;

$R^8$ is cyano, $CO_2R^d$, $CON(R^d)_2$, aryl, or substituted aryl; wherein each of the substituents on substituted aryl is independently halogen, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $(CH_2)_{0-4}SO_2R^d$, $(CH_2)_{0-4}C(=O)N(R^d)_2$, $C_2$–$C_8$ alkoxyalkyl, or fluorinated $C_2$–$C_8$ alkoxyalkyl;

$R^9$ is aryl, substituted aryl, heteroaryl, or substituted heteroaryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $(CH_2)_{0-4}SO_2R^d$, $C_2$–$C_8$ alkoxyalkyl, or fluorinated $C_2$–$C_8$ alkoxyalkyl; and wherein each of the substitutents on substituted heteroaryl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^{10}$ is hydrogen, $C_1$–$C_6$ alkyl, or fluorinated $C_1$–$C_6$ alkyl;

$R^{12}$ is hydrogen, $C_1$–$C_4$ alkyl, or fluorinated $C_1$–$C_4$ alkyl;

each $X^1$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

D is absent, $[C(R^aR^b)]_{1-4}$, $O[C(R^aR^b)]_{1-2}$, $[C(R^aR^b)]_{1-2}O$, $C(R^a)=C(R^b)$, $C(R^aR^b)-C(R^a)=C(R^b)$, or $C(R^a)=C(R^b)-C(R^aR^b)$;

E is absent, $C(=O)$, $C(=O)O$, $N(SO_2R^c)C(R^aR^b)$, $N(R^c)C(=O)$, or $N(R^c)C(=O)O$, provided that (i) when E is absent, D is $[C(R^aR^b)]_{2-4}$, $O[C(R^aR^b)]_{1-2}$, $[C(R^aR^b)]_{1-20}$, $C(R^a)=C(R^b)$, $C(R^aR^b)-C(R^a)=C(R^b)$, or $C(R^a)=C(R^b)-C(R^aR^b)$; (ii) when E is $C(=O)$ or $C(=O)O$, D is $C(R^aR^b)$ or $C(R^aR^b)C(R^aR^b)$; and (iii) when E is $N(SO_2R^c)C(R^aR^b)$, $N(R^c)C(=O)$ or $N(R^c)C(=O)O$, D is absent or $C(R^aR^b)$;

L is $[C(R^aR^b)]_{1-2}$;

M is $C(=O)$, $C(=O)O$, or $N(R^c)C(=O)$;

each $X^2$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

$R^a$, $R^b$, and $R^c$ are each independently hydrogen, $C_1$–$C_4$ alkyl, or fluorinated $C_1$–$C_4$ alkyl;

$R^d$ is hydrogen, $C_1$–$C_6$ alkyl, or fluorinated $C_1$–$C_6$ alkyl;

m is an integer from 1 to 4;

p and q are each independently integers from 0 to 3;

r is an integer equal to 0 or 1;

s1 is an integer from 0 to 5;

s2 is an integer from 0 to 4; and t is an integer from 0 to 4;

and provided that when Q is of formula (q2), then $R^9$ is substituted aryl, heteroaryl, or substituted heteroaryl, and either (i) each of

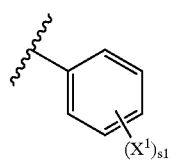

and $R^5$ is independently substituted phenyl or (ii)

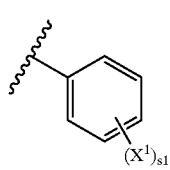

is substituted phenyl and $R^5$ is heterocyclic or substituted heterocyclic;

further provided that when Q is of formula (q6), then

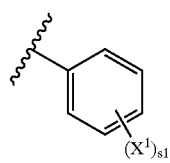

is not phenyl and $R^5$ is substituted phenyl; and further provided that when Q is of formula (q7), then

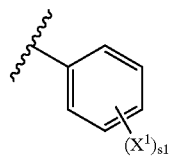

is not phenyl, $R^5$ is substituted phenyl, and m is 2;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes arylhydantoin derivatives of Formula (I) above. These compounds and their pharmaceutically acceptable salts are useful as alpha 1a antagonists.

A first embodiment of the present invention is a compound of Formula (I), wherein one of $R^1$ and $R^2$ is hydrogen and the other of $R^1$ and $R^2$ is hydrogen, $C_1$–$C_6$ alkyl, or $C_3$–$C_8$ cycloalkyl;

one of $R^3$ and $R^4$ is hydrogen and the other of $R^3$ and $R^4$ is hydrogen, $C_1$–$C_6$ alkyl, or $C_3$–$C_8$ cycloalkyl;

$R^5$ is $C_1$–$C_6$ alkyl, phenyl, napthyl, mono- or di- substituted phenyl or naphthyl, heterocyclic, or mono- or di-substituted heterocyclic; wherein heterocyclic is pyridyl, thienyl, or furanyl;

$R^6$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $C_2$–$C_8$ alkoxyalkyl, or fluorinated $C_2$–$C_8$ alkoxyalkyl;

each $R^7$ is independently hydrogen, $C_1$–$C_4$ alkyl, or $CO_2R^d$;

$R^8$ is cyano, $CO_2R^d$, $CON(R^d)_2$, phenyl, or mono- or di- or tri-substituted phenyl;

$R^9$ is phenyl, naphthyl, substituted phenyl, or substituted naphthyl; or pyridyl, pyrazinyl, thienyl, or furanyl; or substituted pyridyl, pyrazinyl, thienyl, or furanyl;

$R^d$ is hydrogen, $C_1$–$C_4$ alkyl, or $(CH_2)_{0-4}CF_3$;

m is an integer from 1 to 3;

p and q are each integers from 0 to 3, provided that the sum of m and n is an integer less than or equal to 3;

s1 is an integer from 0 to 3;

s2 is an integer from 0 to 2;

t is an integer from 0 to 2;

and all other variables are as originally defined above;

and provided that when Q is of formula (q2), then $R^9$ is substituted phenyl or substituted naphthyl; or pyridyl, pyrazinyl, thienyl, or furanyl, or substituted pyridyl, pyrazinyl, thienyl, or furanyl; and either (i) each of

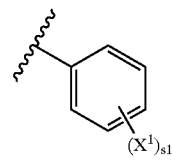

and $R^5$ is independently substituted phenyl, or (ii)

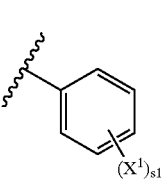

is substituted phenyl and $R^5$ is heterocyclic or substituted heterocyclic;

or a pharmaceutically acceptable salt thereof.

A second embodiment of the present invention is a compound of Formula (I) wherein Q is

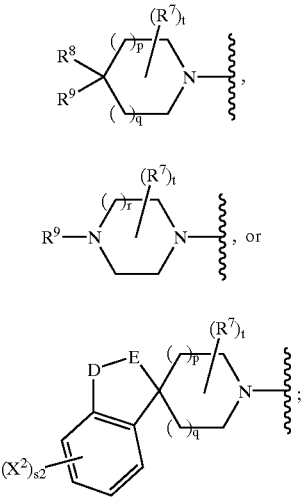

and all other variables are as defined in the first embodiment;

and provided that when Q is of formula (q2), then $R^9$ is substituted phenyl or substituted naphthyl; or pyridyl, pyrazinyl, thienyl, or furanyl; or substituted pyridyl, pyrazinyl, thienyl, or furanyl; and either (i) each of

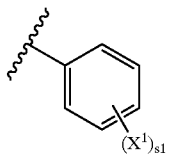

and $R^5$ is independently substituted phenyl, or (ii)

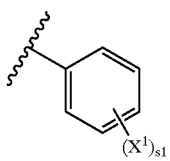

is substituted phenyl and $R^5$ is heterocyclic or substituted heterocyclic;

or a pharmaceutically acceptable salt thereof.

A first class of the present invention is a compound of Formula (II):

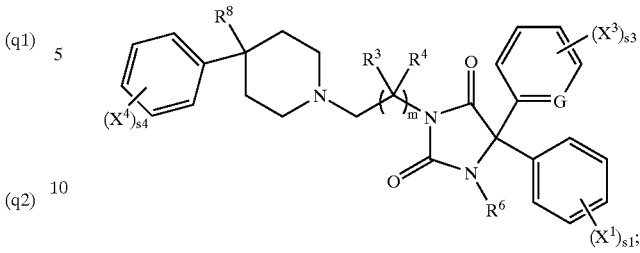

wherein
G is N or $CX^3$;
one of $R^3$ and $R^4$ is hydrogen and the other of $R^3$ and $R^4$ is hydrogen or $C_1$–$C_4$ alkyl;
$R^6$ is hydrogen, methyl, ethyl, $CH_2OCH_3$, $CH_2OCH_2CH_3$, $CH_2CO_2CH_3$, or $CH_2CO_2CH_2CH_3$;
$R^8$ is cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;
each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;
each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;
each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;
$R^d$ is hydrogen, methyl, ethyl, or $CF_3$;
m is an integer equal to 2 or 3;
s1 is an integer from 0 to 3;
s3 is an integer from 0 to 3; and
s4 is an integer from 0 to 2;
or a pharmaceutically acceptable salt thereof.

A second class of the present invention is a compound of Formula (III):

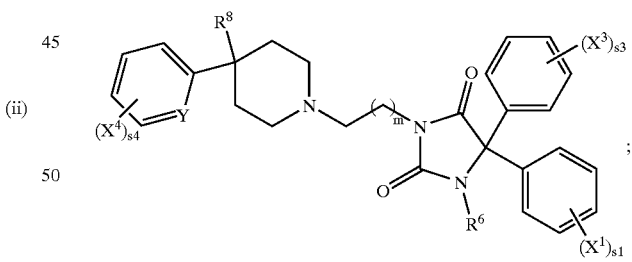

wherein
Y is N or $CX^4$;
$R^6$ is hydrogen, methyl, ethyl, $CH_2OCH_3$, $CH_2OCH_2CH_3$, $CH_2CO_2CH_3$, or $CH_2CO_2CH_2Ch_3$;
$R^8$ is cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^d$ is hydrogen, methyl, ethyl, or $CF_3$;

m is an integer equal to 2 or 3;

s1 is an integer from 0 to 3;

s3 is an integer from 0 to 3; and s4 is an integer from 0 to 2;

or a pharmaceutically acceptable salt thereof.

A subclass of the preceding class is a compound of Formula (IV):

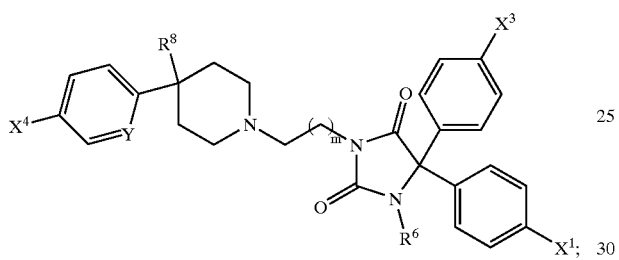

(IV)

wherein $R^6$ is hydrogen, methyl, $CH_2OCH_3$, or $CH_2CO_2CH_2CH_3$;

$R^8$ is cyano;

$X^1$ is hydrogen, fluorine, chlorine, cyano, methyl, ethyl, methoxy, ethoxy, $CF_3$, or $OCF_3$;

$X^3$ is hydrogen, fluorine, chlorine, cyano, methyl, ethyl, methoxy, ethoxy, $CF_3$, or $OCF_3$;

each $X^4$ is independently hydrogen, fluorine, chlorine, cyano, methyl, ethyl, methoxy, ethoxy, $CF_3$, or $OCF_3$; and m is an integer equal to 2 or 3;

or a pharmaceutically acceptable salt thereof.

Exemplary of compounds of the second embodiment are compounds selected from the group consisting of (+/−)-3-[2-methyl-3-(4-phenyl-4-cyanopiperidin-1-yl)propyl]-5,5-bis(4-methylphenyl)-imidazolin-2,4-dione;

(+/−)-3-{3-[4-(2-methylphenyl)-4-cyanopiperidin-1-yl]propy}-5-(4-methylphenyl)-5-(2-pyridyl)-imidazolin-2,4-dione;

3-[3-(4-phenyl-4-cyanopiperidin-1-yl)propyl]-5,5-bis(4-methylphenyl)-imidazolin-2,4-dione;

3-{3-[4-phenyl-4-cyanopiperidin-1-yl]propyl}-5,5-bis(4-chlorophenyl)-imidazolin-2,4-dione;

(+/−)-3-{3-[4-phenyl-4-cyanopiperidin-1-yl]propyl}-5-(4-methylphenyl)-5-phenyimidazolin-2,4-dione;

3-{3-[4-(2-methylphenyl)-4-cyanopiperidin-1-yl]propyl}-5,5-bis(4-methylphenyl)-imidazolin-2,4-dione;

3-{3-[4-(2-methylphenyl)-4-cyanopiperidin-1-yl]propyl}-5,5-bis(4-fluorophenyl)-imidazolin-2,4-dione;

3-{3-[4-(2-pyridyl)piperidin-1-yl]propyl}-5,5-bis(4-methylphenyl)-imidazolin-2,4dione;

3-[3-(4-phenyl-4-cyanopiperidin-1-yl)propyl]-5,5-bis(phenyl)-imidazolin-2,4-dione; (15)

(3-{3-[4-(4-fluoro-2-cyanophenyl)piperidin-1-yl]propyl}-5,5-bis(4-methylphenyl)-imidazolin-2,4-dione;

1-methyl-3-{3-[4-(2-methylphenyl)-4-cyanopiperidin-1-yl]propyl}-bis-5,5-(4-methylphenyl)-imidazolin-2,4-dione;

1-ethoxycarbonylmethyl-3-{3-[4-(2-methylphenyl )-4-cyanopiperidin-1-yl]propyl}-bis-5,5-(4-methylphenyl)-imidazolin-2,4-dione;

1-methoxymethyl-3-{3-[4-(2-methylphenyl)-4-cyanopiperidin-1-yl]propyl}-5,5-bis(4-methylphenyl)-imidazolin-2,4-dione;

and pharmaceutically acceptable salts thereof.

A preferred aspect of the present invention is 3-[3-(4-phenyl-4-cyanopiperidin-1-yl)propyl]-5,5-bis(4-methylphenyl)-imidazolin-2,4-dione, or a pharmaceutically acceptable salt thereof.

A third class of the present invention is a compound of Formula (V):

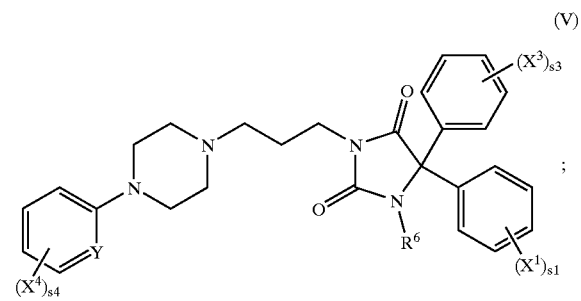

(V)

wherein

Y is N or $CX^4$;

$R^6$ is hydrogen, methyl, or ethyl;

each $X^1$ is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $C(=O)N(R^d)_2$, $(CH_2)_{1-4}OCH_3$, or $(CH_2)_{1-4}OCF_3$;

$R^d$ is hydrogen, methyl, ethyl, or $CF_3$;

s1 is an integer from 0 to 3;

s3 is an integer from 0 to 3; and s4 is an integer equal to 1 or 2;

and provided that when Y is $CX^4$, then at least one $X^4$ is not hydrogen;

or a pharmaceutically acceptable salt thereof.

A subclass of the preceding class is a compound of Formula (VI):

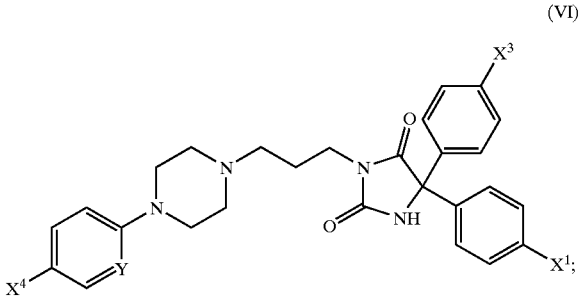

(VI)

wherein $X^1$ is fluorine, chlorine, cyano, methyl, ethyl, methoxy, ethoxy, $CF_3$, or $OCF_3$;

$X^3$ is fluorine, chlorine, cyano, methyl, ethyl, methoxy, ethoxy, $CF_3$, or $OCF_3$; and each $X^4$ is independently hydrogen, fluorine, chlorine, cyano, methyl, ethyl, methoxy, ethoxy, $C(=O)NH_2$, $CF_3$, $OCF_3$, or $OCH_2CF_3$;

or a-pharmaceutically acceptable salt thereof.

Also exemplary of compounds of the second embodiment are compounds selected from the group consisting of 3-{3-[4-(2-cyanophenyl)-piperazin-1-yl]propyl}-5,5-bis(4-methylphenyl)-imidazolin2,4-dione;

3-{3-[4-(2-aminocarbonylphenyl)-piperazin-1-yl]propyl}-5,5-bis(4-methylphenyl)-imidazolin-2,4-dione;

3-{3-(4-[4-fluoro-2-(2,2,2-trifluoroethoxy)phenyl]-piperazin-1-yl)propyl}-5,5-bis(4-methylphenyl)-imidazolin-2,4-dione;

and pharmaceutically acceptable salts thereof.

A fourth class of the present invention is a compound of Formula (VII):

(VII)

structure VII wherein $R^6$ is hydrogen, methyl, or ethyl;

D is absent, $[C(R^aR^b)]_{1-4}$, $O[C(R^aR^b)]_{1-2}$, $[C(R^aR^b)]_{1-2}O$, $C(R^a)=C(R^b)$, $C(R^aR^b)-C(R^a)=C(R^b)$, or $C(R^a)=C(R^b)-C(R^aR^b)$;

E is absent, $C(=O)$, $C(=O)O$, $N(R^c)C(=O)$, or $N(R^c)C(=O)O$; provided that (i) when E is absent, D is $[C(R^aR^b)]_{2-4}$, $O[C(R^aR^b)]_{1-2}$, $[C(R^aR^b)]_{1-2}O$, $C(R^a)=C(R^b)$, $C(R^aR^b)-C(R^a)=C(R^b)$, or $C(R^a)=C(R^b)-C(R^aR^b)$; (ii) when E is $C(=O)$ or $C(=O)O$, D is $C(R^aR^b)$; and (iii) when E is $N(R^c)C(=O)$ or $N(R^c)C(=O)O$, D is absent;

each $X^1$ is independently hydrogen, halogen, cyano, $C_1-C_4$ alkyl, $(CH_2)_{0-4}CF_3$, $C_1-C_4$ alkoxy, $OCF_3$, $OCH_2CF_3$, $(CH_2)_{0-4}CO_2R^d$, $(CH_2)_{1-4}OCH_3$, or $(CH_2)_{1-4}OCF_3$;

each $X^2$ is independently hydrogen, halogen, cyano, $C_1-C_4$ alkyl, $(CH_2)_{0-4}OCF_3$, $C_1-C_4$ alkoxy, $OCF_3$, $OCH_2CF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1-C_4$ alkyl, $(CH_2)_{0-4}CF_3$, $C_1-C_4$ alkoxy, $OCF_3$, $OCH_2CF_3$, $(CH_2)_{0-4}CO_2R^d$, $(CH_2)_{1-4}OCH_3$, or $(CH_2)_{1-4}OCF_3$;

$R^a$, $R^b$, and $R^c$ are each independently hydrogen, $C_1-C_4$ alkyl, or fluorinated $C_1-C_4$ alkyl;

$R^d$ is hydrogen, methyl, ethyl, or $CF_3$;

m is an integer equal to 2 or 3;

s1 is an integer from 0 to 3;

s2 is an integer from 0 to 2; and s3 is an integer from 0 to 3;

or a pharmaceutically acceptable salt thereof.

A subclass of the preceding class is a compound of Formula (VIII):

(VIII)

structure VIII wherein

D is absent, $CH_2$, $CH_2CH_2$, or $CH=CH$;

E is absent, $C(=O)$, $C(=O)O$, $N(R^c)C(=O)$, or $N(R^c)C(=O)O$; provided that (i) when E is absent, D is $CH_2CH_2$ or $CH=CH$; (ii) when E is $C(=O)$ or $C(=O)O$, D is $CH_2$; and (iii) when E is $N(R^c)C(=O)$ or $N(R^c)C(=O)O$, D is absent;

$X^1$ is hydrogen, fluorine, chlorine, cyano, methyl, ethyl, $CF_3$, methoxy, ethoxy, $OCF_3$, or $OCH_2CF_3$;

each $X^2$ is independently hydrogen, fluorine, chlorine, cyano, methyl, ethyl, $CF_3$, methoxy, ethoxy, $OCF_3$, $CH_2CO_2CH_3$, $CH_2OCH_3$, or $CH_2OCF_3$;

$X^3$ is hydrogen, fluorine, chlorine, cyano, methyl, ethyl, $CF_3$, methoxy, ethoxy, $OCF_3$, or $OCH_2CF_3$;

$R^c$ is hydrogen, methyl, ethyl, $CF_3$, or $CH_2CF_3$; and m is an integer equal to 2 or 3;

or a pharmaceutically acceptable salt thereof.

Also exemplary of compounds of the second embodiment are compounds selected from the group consisting of 3-{3-(spiro[1H-indeno-1,4'-piperidin]-1'-yl)propyl}-5,5-bis(4-methylphenyl)-imidazolin-2,4-dione;

3-{3-(1-methyl-6-chloro-spiro[4H-3,1-benzoxazine-4,4'-piperidin]-2(1H)-on-1'-yl)propyl}-5,5-bis(4-methylphenyl)-imidazolin-2,4-dione;

3-{3-(1-methyl-6-chloro-spiro[4H-3,1-benzoxazine-4,4'-piperidin]-2(1H)-on-1'-yl)propyl}-5,5-bis(4-chlorophenyl)-imidazolin-2,4-dione;

3-{3-(6-chloro-spiro[4H-3,1-benzoxazine-4,4'-piperidin]-2(1H)-on-1'-yl)propyl}-5,5-bis(4-methylphenyl)-imidazolin-2,4-dione;

3-{3-(spiro[4H-3,1-benzoxazine-4,4'-piperidin]-2(1H)-on-1'-yl)propyl}-5,5-bis(4-methylphenyl)-imidazolin-2,4-dione;

3-{3-(1-methyl-spiro[4H-3,1-benzoxazine-4,4'-piperidin]-2(1H)-on-1'-yl)propyl}-5,5-bis(4-methylphenyl)-imidazolin-2,4-dione;

3-{4-(spiro[indeno-1,4'-piperidin]-1'-yl)butyl}-5,5-bis(4-methylphenyl)-imidazolin-2,4-dione;

3-{4-(2,3-dihydro-spiro[indeno-1,4'-piperidin]-2(3H)-on-1'-yl)butyl}-5,5-bis(4-methylphenyl)-imidazolin-2,4-dione;

3-{3-(2,3-dihydro-spiro[indeno-1,4'-piperidin]-2(3H)-on-1'-yl)propyl}-5,5-bis(4-methylphenyl)-imidazolin-2,4-dione;

3-{3-(1-methyl-spiro[3H-indole-3,4'-piperidin]-2(1H)-on-1'-yl)propyl}-5,5-bis(4-methylphenyl)-imidazolin-2,4-dione;

3-{3-(2,3-dihydro-spiro[indeno-1,4'-piperidin]-1'-yl)propyl}-5,5-bis(4-methylphenyl)-imidazolin-2,4-dione;

3-{3-[1-(2,2,2-trifluoroethyl)-6-chloro-spiro[4H-3,1-benzoxazine-4,4'-piperidin]-2(1H)-on-1'-yl]propyl}-5,5-bis(4-methylphenyl)-imidazolin-2,4-dione;

3-{3-(6-fluoro-spiro[4H-3,1-benzoxazine-4,4'-piperidin]-2 (1H)-on-1'-yl)propyl}-5,5-bis(4-methylphenyl)-imidazolin-2,4-dione;

3-{3-(spiro[3H-indole-3,4'-piperidin]-2(1H)-on-1'-yl) propyl}-5,5-bis(4-methylphenyl)-imidazolin-2,4-dione;

and pharmaceutically acceptable salts thereof.

A fifth class of the invention is a compound of Formula (I), wherein Q is a group of formula (q1);

$R^5$ is $C_1$–$C_6$ alkyl;

$R^8$ is cyano, $CO_2Rd$, $CON(R^d)_2$, phenyl, or mono- or di- or tri-substituted phenyl;

m is an integer equal to 2 or 3;

and all other variables are as defined in the second embodiment.

or a pharmaceutically acceptable salt.

Still other compounds which are exemplary of the second embodiment are compounds selected from the group consisting of (+/−)-3-{3-[4-phenyl-4-cyanopiperidin-1-yl]propyl}-5-methyl-5-phenyl-imidazolin-2,4-dione;

(+/−)-3-{3-[4-(2-methylphenyl)-4-cyanopiperidin-1-yl] propyl}-5-isopropyl-5-(4-methylphenyl)-imidazolin-2,4-dione;

(+/−)-3-{3-[4-(2-methylphenyl)-4-cyanopiperidin-1-yl] propyl}-5-pentyl-5-(4-methylphenyl)-imidazolin-2,4-dione;

(+/−)-3-{3-[4-(2-methylphenyl)-4-cyanopiperidin-1-yl] propyl}-5-pentyl-5-(3,4-difluoro-phenyl)-imidazolin-2,4-dione;

(+/−)-3-{3-[4-(2-methylphenyl)-4-cyanopiperidin-1-yl] propyl}-5-pentyl-5-(4-chlorophenyl)-imidazolin-2,4-dione;

and pharmaceutically acceptable salts thereof.

A third embodiment of the present invention is a compound of Formula (IX):

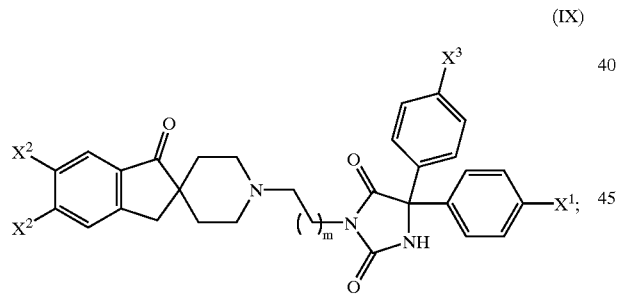

(IX)

wherein
$X^1$ is fluorine, chlorine, cyano, methyl, ethyl, $CF_3$, methoxy, ethoxy, $OCF_3$, or $OCH_2CF_3$;

each $X^2$ is independently hydrogen, fluorine, chlorine, cyano, methyl, ethyl, $CF_3$, methoxy, ethoxy, $OCF_3$, $CH_2CO_2CH_3$, $CH_2OCH_3$, or $CH_2OCF_3$;

$X^3$ is fluorine, chlorine, cyano, methyl, ethyl, $CF_3$, methoxy, ethoxy, $OCF_3$, or $OCH_2CF_3$; and m is an integer equal to 2 or 3;

or a pharmaceutically acceptable salt thereof.

Exemplary of compounds embraced by the third embodiment is 3-{3-(2,3-dihydro-spiro[indeno-2,4'-piperidin]-1 (2H)-on-1'-yl)propyl}-5,5-bis(4-methylphenyl)-imidazolin-2,4-dione, or a pharmaceutically acceptable salt thereof.

A fourth embodiment of the present invention is a compound of Formula (X):

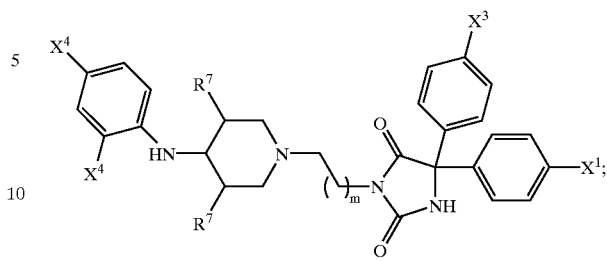

(X)

wherein
$X^1$ is hydrogen, fluorine, chlorine, cyano, methyl, ethyl, $CF_3$, methoxy, ethoxy, $OCF_3$, or $OCH_2CF_3$;

$X^3$ is hydrogen, fluorine, chlorine, cyano, methyl, ethyl, $CF_3$, methoxy, ethoxy, $OCF_3$, or $OCH_2CF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $R^7$ is independently hydrogen, methyl, ethyl, $CO_2CH_3$, or $CO_2CH_2CH_3$; and m is an integer equal to 2 or 3;

or a pharmaceutically acceptable salt thereof.

Exemplary of compounds embraced by the fourth embodiment is (+/−)-3{-3-[4-(cis-2-chlorophenylamino-3-methoxycarbonylpiperidin-1-yl]propyl}-5,5-bis(4-methylphenyl)-imidazolin-2,4-dione, or a pharmaceutically acceptable salt thereof.

A fifth embodiment of the present invention is a compound of Formula (XI):

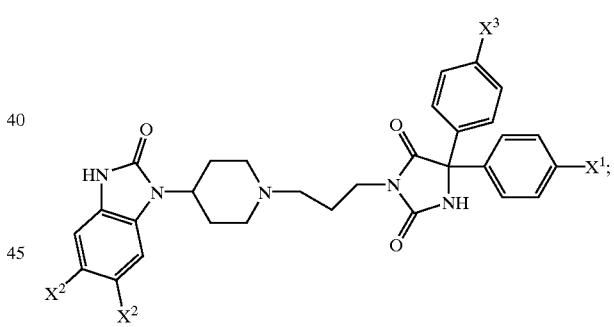

(XI)

wherein
$X^1$ is fluorine, chlorine, cyano, methyl, ethyl, $CF_3$, methoxy, ethoxy, $OCF_3$, or $OCH_2CF_3$;

each $X^2$ is independently hydrogen, fluorine, chlorine, cyano, methyl, ethyl, $CF_3$, methoxy, ethoxy, $OCF_3$, $CH_2CO_2CH_3$, $CH_2OCH_3$, or $CH_2OCF_3$; and $X^3$ is fluorine, chlorine, cyano, methyl, ethyl, $CF_3$, methoxy, ethoxy, $OCF_3$, or $OCH_2CF_3$;

or a pharmaceutically acceptable salt thereof.

Exemplary of compounds embraced by the fifth embodiment is 3-{3-[4-(5-chloro-2-oxo-1-benzimidazolinyl) piperidin-1-yl]propyl}-5,5-bis(4-methylphenyl)-imidazolin-2,4-dione, or a pharmaceutically acceptable salt thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a therapeutically effective amount of a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see Vatz, *Headache* (1997), 37: 107–108) and cardiac arrhythmia.

The present invention also includes a method of preventing or treating prostatic cancer which comprises administering to a subject in need of prevention or treatment thereof a therapeutically effective amount of a combination comprising any of the compounds (or compositions) described above and a testosterone 5-alpha reductase inhibitor. The testosterone 5-alpha reductase inhibitor is suitably finasteride.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an -O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_2$–$C_8$ alkoxyalkyl" means a linear or branched $C_1$–$C_6$ alkyl group as defined above having as a substituent a $C_1$–$C_6$ alkoxy group as defined above, wherein the alkoxyalkyl group has a total of from 2 to 8 carbon atoms. Representative examples of suitable alkoxyalkyl groups include, but are not limited to, the $C_1$–$C_6$ alkoxy-substituted methyl groups (methoxymethyl, ethoxymethyl, n-propoxymethyl, isopropoxymethyl, and the butyloxymethyl, pentyloxymethyl, and hexyloxymethyl isomers), and the $C_1$–$C_6$ alkoxy-substituted ethyl groups. Other suitable alkoxyalkyl groups include the series $(CH_2)_{1-6}OCH_3$, $(CH_2)_{1-4}OCH_3$, $(CH_2)_{1-6}OCH_2CH_3$, and $(CH_2)_{1-4}OCH_2CH_3$.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). The term "$C_3$–$C_6$ cycloalkyl" refers to a cyclic ring selected from cyclopropyl, cyclobutyl, cyclopentyl, and cyclohexyl. "$C_4$–$C_6$ cycloalkyl" has an analogous meaning.

The term "halogen" (which may alternatively be referred to as "halo") refers to fluorine, chlorine, bromine and iodine (alternatively, fluoro, chloro, bromo, and iodo).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. The terms "fluorinated $C_3$–$C_7$ cycloalkyl" and "fluorinated $C_3$–$C_6$ cycloalkyl" have analogous meanings. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. The term "fluorinated $C_1$–$C_4$ alkoxy" has an analogous meaning.

Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "fluorinated $C_2$–$C_8$ alkoxyalkyl" means $C_2$–$C_8$ alkoxyalkyl as defined above, wherein either or both the alkoxy moiety and the alkyl moiety has one or more fluorine substituents. Representative examples of suitable fluorinated alkoxyalkyl groups include, but are not limited to, the $C_1$–$C_6$ fluoroalkoxy-substituted methyl groups (e.g., fluoromethoxymethyl, 2-fluoroethoxymethyl, and 3-fluoro-n-propoxymethyl), $C_1$–$C_6$ difluoroalkoxymethyl groups (e.g., difluoromethoxymethyl and 2,2-difluoroethoxymethyl), $C_1$–$C_6$ trifluoroalkoxy-substituted methyl groups (e.g., trifluoromethoxymethyl and 2,2,2-trifluoroethoxymethyl), $C_1$–$C_6$ alkoxy-substituted fluoromethyl groups (e.g., methoxy- or ethoxy-fluoromethyl), and $C_1$–$C_6$ alkoxy-substituted difluoromethyl groups (e.g., methoxy- or ethoxy-difluoromethyl). Other suitable fluorinated alkoxyalkyl groups include the series $(CH_2)_{1-6}OCF_3$, $(CH_2)_{1-4}OCF_3$, $(CH_2)_{1-6}OCH_2CF_3$, and $(CH_2)_{1-4}OCH_2CF_3$.

The term "heterocyclic" (which may alternatively be referred to as "heterocycle") refers to a stable 5- to 7-membered monocyclic ring system which may be saturated or unsaturated; which consists of carbon atoms and from one to three heteroatoms selected from N, O or S, and wherein the nitrogen and sulfur heteroatoms may optionally be oxidized, and the nitrogen heteroatom may optionally be quaternized. The heterocyclic ring may be attached at any single heteroatom or carbon atom, provided that attachment results in the creation of a stable structure. Suitable heterocyclic groups include, but are not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxadiazolyl, triazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. Morpholino is the same as morpholinyl.

The term "thienyl," as used herein, refers to the group

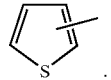

The term "substituted heterocyclic" refers to a heterocyclic group as defined above having one or more subsituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—($C_1$–$C_6$ alkyl)amino, N,N-di-($C_1$–$C_6$ alkyl)amino, aryl (defined below), carboxy, $C_1$–$C_6$ alkoxycarbonyl, sulfonamido, sulfonyl, and the like.

The term "aryl" refers herein to aromatic mono- and poly-carbocyclic ring systems, wherein the carbocyclic rings in the polyring systems may be fused or attached via a single ring carbon. Suitable aryl groups include, but are not limited to, phenyl, naphthyl, and biphenylenyl.

"Substituted aryl" refers to an aryl group as defined above having one or more substituents independently selected from halogen, cyano, $C_1$–$C_6$ alkyl, fluorinated $C_1$–$C_6$ alkyl, $C_1$–$C_6$ alkoxy, fluorinated $C_1$–$C_6$ alkoxy, $C_2$–$C_8$ alkoxyalkyl, fluorinated $C_2$–$C_8$ alkoxyalkyl, $C_3$–$C_8$ cycloalkyl, fluorinated $C_3$–$C_8$ cycloalkyl, amino, N—$C_1$–$C_6$ alkylamino, N,N-di-($C_1$–$C_6$)alkylamino, aryl, carboxy, $C_1$–$C_6$ alkoxycarbonyl, sulfonamido, sulfonyl, and the like.

The term "heteroaryl" refers to the subset of heterocycles as heretofore defined which are aromatic heterocyclic ring systems, including, but not limited to, pyridyl, pyrazinyl, thienyl, thiazolyl, furanyl, imidazolyl, pyrazolyl, triazolyl, oxazolyl, oxadiazolyl, thiazolyl, and thiadiazolyl.

"Substituted heteroaryl" refers to heteroaryl groups as defined above having one or more substituents as defined above.

The term "substituted" includes mono- and poly-substitution by a named substituent to the extent such single and multiple substitution is chemically allowed.

The expression "E is absent" means that E is replaced by a bond connecting the atoms/moieties to which E would otherwise be attached; e.g., when E is absent in (q4), then (q4) may be represented as:

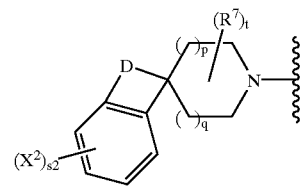

The expression "D is absent" has a meaning analogous to that of "E is absent", as just described.

It is understood that the definition of a substituent (e.g., $CO_2R^d$) or variable (e.g., $R^d$) at a particular location in a molecule is independent of its definitions at other locations in that molecule. Thus, for example, when $R^8$ is $CO_2R^d$=$CO_2H$, and $R^9$ is substituted phenyl wherein at least one of the substituents is $CO_2R^d$, it is understood that $CO_2R^d$ in $R^9$ can be any one of $CO_2H$, $CO_2Me$, $CO_2Et$, $CO_2Pr$, etc. As another example, the moiety

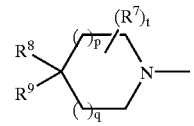

wherein $R^7$ is hydrogen or $C_1$–$C_4$ alkyl, p=1, q=1, and t=2, represents moieties such as

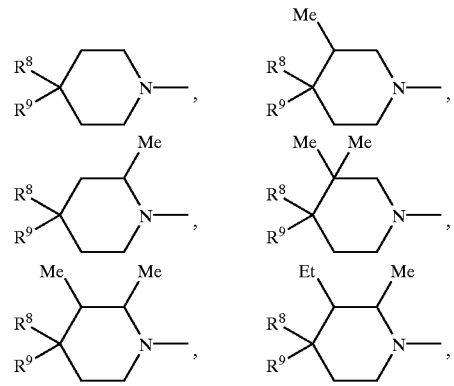

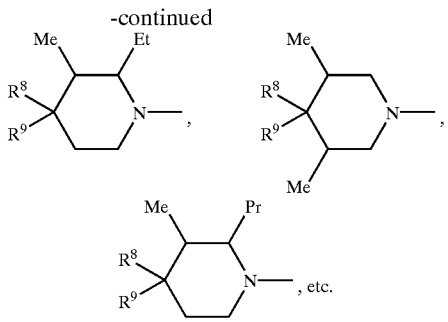

It is also understood that the definition of a substituent or variable at a particular location in a molecule is independent of the definition of another occurrence of the same substituent or variable at the same location. Thus, $C(=O)N(R^d)_2$ represents groups such as $—C(=O)NH_2$, $—C(=O)NHCH_3$, $—C(=O)NHC_2H_5$, $—C(=O)N(CH_3)C_2H_5$, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Representative embodiments for the variables and substituents set forth in Formula (1) include the following:

One of $R^1$ and $R^2$ is hydrogen or fluorine and the other of $R^1$ and $R^2$ is hydrogen, fluorine, $C_1$–$C_6$ alkyl, or $C_3$–$C_8$ cycloalkyl. In other embodiments, each of $R^1$ and $R^2$ is hydrogen, fluorine, or $C_1$–$C_4$ alkyl; or is hydrogen, fluorine, methyl, or ethyl; or is hydrogen or fluorine; or is hydrogen; or is fluorine.

One of $R^3$ and $R^4$ is hydrogen or fluorine and the other of $R^3$ and $R^4$ is hydrogen, fluorine, $C_1$–$C_6$ alkyl, or $C_3$–$C_8$ cycloalkyl. In other embodiments, each of $R^3$ and $R^4$ is hydrogen, fluorine, or $C_1$–$C_4$ alkyl; or is hydrogen, fluorine, methyl, or ethyl; or is hydrogen or fluorine; or is hydrogen; or is fluorine.

In another embodiment, one of $R^1$ and $R^2$ is hydrogen and the other is fluorine, and one of one of $R^3$ and $R^4$ is hydrogen and the other is fluorine (i.e., the chain linking Q to the spirohydantoin moiety is $(CHF)_{m+1}$.)

$R^5$ is $C_1$–$C_6$ alkyl, phenyl, napthyl, mono- or di- substituted phenyl or naphthyl, heterocyclic, or mono- or di-substituted heterocyclic, wherein heterocyclic is pyridyl, thineyl, or furanyl. In one embodiment, $R^5$ is $C_1$–$C_5$ alkyl; or is methyl, isopropyl, propyl, or n-pentyl. In another embodiment, $R^5$ is substituted phenyl.

When $R^5$ is substituted aryl (e.g., substituted phenyl), each of the substituents on substituted aryl is independently halo, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, $(CH_2)_{0-4}CO_2R^d$, $(CH_2)_{0-4}C(=O)N(R^d)_2$, $C_2$–$C_8$ alkoxyalkyl, or fluorinated $C_2$–$C_8$ alkoxyalkyl; or each is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or each is independently fluorine, chlorine, cyano, methyl, ethyl, methoxy, ethoxy, $CF_3$ or $OCF_3$.

When $R^5$ is substituted heterocyclic (e.g., substituted pyridyl), each of the substituents on substituted heterocyclic is independently halogen, cyano, $C_1$–$C_4$ alkyl, fluorinated $C_1$–$C_4$ alkyl, $C_1$–$C_4$ alkoxy, fluorinated $C_1$–$C_4$ alkoxy, ($CH_2)_{0-4}CO_2R^d$, $(CH_2)_{0-4}C(=O)N(R^d)_2$, $C_2$–$C_8$ alkoxyalkyl, fluorinated $C_2$–$C_8$ alkoxyalkyl, or phenyl; or each is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or each is independently fluorine, chlorine, cyano, methyl, ethyl, methoxy, ethoxy, $CF_3$ or $OCF_3$.

In still another embodiment, $R^5$ is

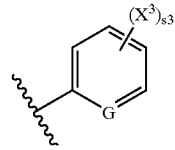

wherein G is N or $CX^3$; each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; and s3 is an integer from 0 to 3. In one aspect of this embodiment, G is $CX^3$; and each $X^3$ is independently hydrogen, fluorine, chlorine, cyano, methyl, ethyl, $CF_3$, methoxy, ethoxy, $OCF_3$, or $OCH_2CF_3$. In another aspect of this embodiment, $R^5$ is

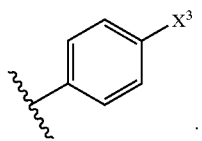

$R^6$ is hydrogen, $C_1$–$C_4$ alkyl, fluorinated $C_1$–$C_4$ alkyl, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $C_2$–$C_8$ alkoxyalkyl, or fluorinated $C_2$–$C_8$ alkoxyalkyl; or is hydrogen, $C_1$–$C_4$ alkyl, $(CH_2)_{1-3}CF_3$, $C_3$–$C_6$ cycloalkyl, fluorinated $C_3$–$C_6$ cycloalkyl, $(CH_2)_{1-2}CO_2R^d$, $(CH_2)_{1-2}C(=O)N(R^d)_2$, $(CH_2)_{1-3}OCH_3$, or $(CH_2)_{1-3}OCF_3$: or is hydrogen, $C_1$–$C_4$ alkyl, or $(CH_2)_{1-3}CF_3$; or is hydrogen, methyl, or ethyl; or is hydrogen.

Each $R^7$ is a substituent connected to a ring atom other than $C(R^8R^9)$, spiro substituted carbon, or N and is independently hydrogen, methyl, or ethyl; or is hydrogen.

$R^8$ is cyano, $CO_2R^d$, $CON(R^d)_2$, phenyl, or substituted phenyl; or is hydrogen, cyano, hydroxy, $CO_2R^d$, $CON(R^d)_2$, phenyl, or mono- or di- or tri-substituted phenyl; or is cyano, $CO_2R^d$, $CON(R^d)_2$, phenyl, or mono- or di-substituted phenyl; or is cyano, $CO_2R^d$, $CON(R^d)_2$, phenyl, or mono- or di-substituted phenyl; or is cyano.

When $R^8$ is substituted aryl (e.g., substituted phenyl), each of the substituents on substituted aryl is independently halogen, cyano, hydroxy, $C_1$–$C_4$ alkyl, fluorinated $C_1$–$C_4$ alkyl, $C_1$–$C_4$ alkoxy, fluorinated $C_1$–$C_4$ alkoxy, $(CH_2)_{0-4}CO_2R^d$, $(CH_2)_{0-4}SO_2R^d$, $(CH_2)_{0-4}C(=O)N(R^d)_2$, $C_2$–$C_8$ alkoxyalkyl, or fluorinated $C_2$–$C_8$ alkoxyalkyl; or each is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or each is independently fluorine, chlorine, cyano, hydroxy, methyl, ethyl, $CF_3$, $OCH_3$, $(CH_2)_{1-2}OCH_3$, or $(CH_2)_{1-2}OCF_3$, $CO_2CH_3$, or $CH_2CO_2CH_3$.

$R^9$ is phenyl, substituted phenyl, naphthyl, or substituted naphthyl; or pyridyl, pyrazinyl, thienyl, or furanyl; or substituted pyridyl, pyrazinyl, thienyl, or furanyl. In another embodiment, $R^9$ is phenyl, naphthyl, pyridyl, pyrazinyl, thienyl, or furanyl, or mono- or di- or tri-substituted phenyl, naphthyl, pyridyl, pyrazinyl, thienyl, or furanyl. In still other embodiments, $R^9$ is phenyl, mono- or di- or tri-substituted phenyl, pyridyl, pyrazinyl, substituted pyridyl, or substituted pyrazinyl; or is phenyl, substituted phenyl, or pyridyl.

When $R^9$ is substituted aryl (e.g., substituted phenyl or substituted naphthyl), each of the substituents is independently halo, cyano, hydroxy, $C_1$–$C_4$ alkyl, fluorinated $C_1$–$C_4$ alkyl, $C_3$–$C_7$ cycloalkyl, fluorinated $C_3$–$C_7$ cycloalkyl, $C_1$–$C_4$ alkoxy, fluorinated $C_1$–$C_4$ alkoxy, $(CH_2)_{0-4}CO_2R^d$, $(CH_2)_{0-4}C(=O)N(R^d)_2$, $(CH_2)_{0-4}SO_2R^d$, $C_2$–$C_8$ alkoxyalkyl, or fluorinated $C_2$–$C_8$ alkoxyalkyl; or each is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $C(=O)N(R^d)_2$, $(CH_2)_{1-4}OCH_3$, or $(CH_2)_{1-4}OCF_3$; or each is independently halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or each is independently fluorine, chlorine, cyano, methyl, ethyl, methoxy, ethoxy, $C(=O)NH_2$, $CF_3$, $OCF_3$, or $OCH_2CF_3$; or each is independently fluorine, chlorine, cyano, methyl, ethyl, methoxy, ethoxy, $CF_3$, or $OCF_3$;

When $R^9$ is substituted heteroaryl (e.g., substituted pyridyl, pyrazinyl, thienyl, or furanyl), each of the substituents is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_4$ alkyl, fluorinated $C_1C_4$ alkyl, $C_3$–$C_7$ cycloalkyl, fluorinated $C_3$–$C_7$ cycloalkyl, $C_1$–$C_4$ alkoxy, fluorinated $C_1$–$C_4$ alkoxy, $(CH_2)_{0-4}CO_2R^d$, $C_2$–$C_8$ alkoxyalkyl, or fluorinated $C_2$–$C_8$ alkoxyalkyl; or each is independently chlorine, fluorine, $C_1$–$C_4$ alkyl, $(CH_2)_{0-3}CF_3$, $C_1$–$C_4$ alkoxy, $OCF_3$, $(CH_2)_{0-4}CO_2CH_3$, $(CH_2)_{1-3}OCH_3$, or $(CH_2)_{1-3}OCF_3$; or is independently halogen or cyano.

In still another embodiment, $R^9$ is

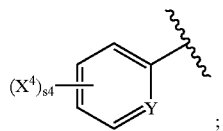

;

wherein Y is N or $CX^4$; each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; and s4 is an integer from 0 to 2. In one aspect of this embodiment, each $X^4$ is independently hydrogen, fluorine, chlorine, cyano, methyl, ethyl, methoxy, ethoxy, $CF_3$, or $OCF_3$. In another aspect of this embodiment, $R^9$ is

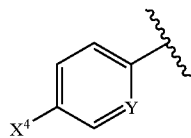

.

$R^{10}$ is hydrogen, $C_1$–$C_4$ alkyl, or $(CH_2)_{0-4}CF_3$; or is hydrogen, methyl, ethyl, $CF_3$, $CH_2CF_3$; or is hydrogen.

$R^{12}$ is hydrogen, $C_1$–$C_4$ alkyl, or $(CH_2)_{0-4}CF_3$; or is hydrogen, methyl, ethyl, $CF_3$, $CH_2CF_3$; or is hydrogen.

Each $X^1$ is independently hydrogen, halogen, cyano, $C_1$–$C_4$ alkyl, $C_3$–$C_7$ cycloalkyl, fluorinated $C_1$–$C_4$ alkyl, fluorinated $C_3$–$C_7$ cycloalkyl, $(CH_2)_{0-4}CO_2R^d$, $(CH_2)_{0-4}C(=O)N(R^d)_2$, $C_1$–$C_4$ alkoxy, fluorinated $C_1$–$C_4$ alkoxy, $C_2$–$C_8$ alkoxyalkyl, or fluorinated $C_2$–$C_8$ alkoxyalkyl; or each is independnetly hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or is independently hydrogen, fluorine, chlorine, cyano, methyl, ethyl, methoxy, ethoxy, $CF_3$, or $OCF_3$; or is independently hydrogen, fluorine, chlorine, or methyl; or is hydrogen or fluorine.

D is absent, $[C(R^aR^b)]_{1-4}$, $C(R^a)=C(R^b)$, $[C(R^aR^b)]_{1-2}O$, or $O[C(R^aR^b)]_{1-2}$; or D is absent, $[C(R^aR^b)]_{1-4}$, or $[C(R^aR^b)]_{1-2}O$; or D is absent or $(CH_2)_{1-4}$.

E is absent, $C(=O)$, $C(=O)O$, $N(SO_2R^c)C(R^aR^b)$, $N(R^c)C(=O)$, or $N(R^c)C(=O)O$, provided that (i) when E is absent, D is $[C(R^aR^b)]_{2-4}$, $C(R^a)=C(R^b)$, or $O[C(R^aR^b)]_{1-2}$; (ii) when E is $C(=O)$ or $C(=O)O$, D is $C(R^aR^b)$ or $C(R^aR^b)C(R^aR^b)$; and (iii) when E is $N(SO_2R^c)C(R^aR^b)$, $N(R^c)C(=O)$, or $N(R^c)C(=O)O$, D is absent or $C(R^aR^b)$.

Groups of formula (q4) include the following, which embody particular combinations of D and E:

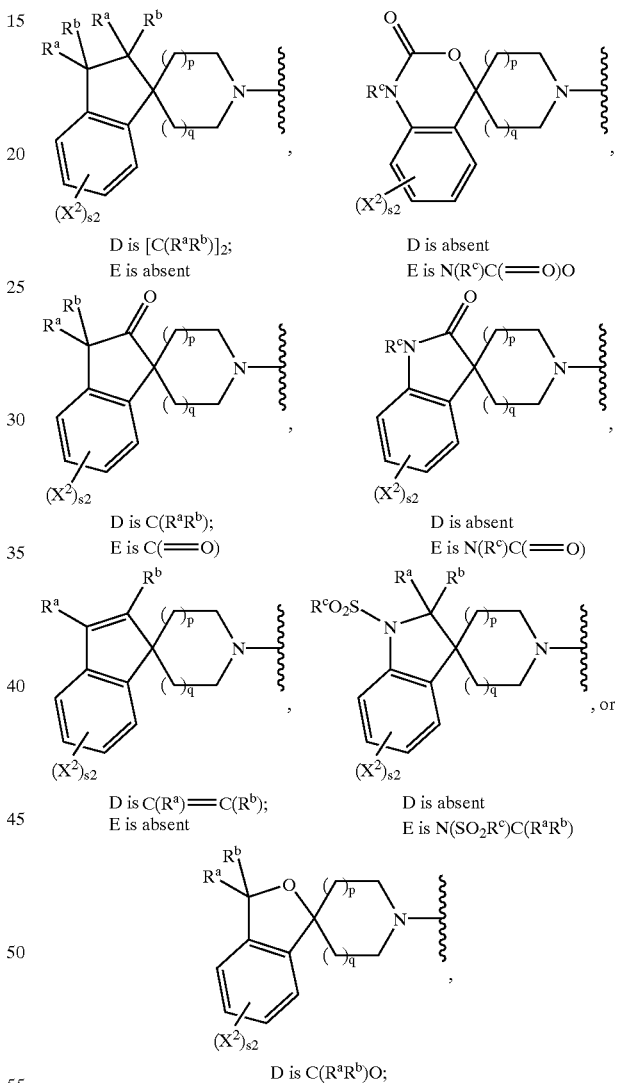

L is $C(R^aR^b)$; or is $CH_2$.

M is $C(=O)$.

Each $x^2$ is independently hydrogen, halogen, cyano, $C_1$–$C_4$ alkyl, $C_3$–$C_7$ cycloalkyl, fluorinated $C_1$–$C_6$ alkyl, fluorinated $C_3$–$C_7$ cycloalkyl, $(CH_2)_{0-4}CO_2R^d$, $(CH_2)_{0-4}C(=O)N(R^d)_2$, $C_1$–$C_4$ alkoxy, fluorinated $C_1$–$C_4$ alkoxy, $C_2$–$C_8$ alkoxyalkyl, or fluorinated $C_2$–$C_8$ alkoxyalkyl; or is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or is independently hydrogen, chlorine, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; or is independently hydrogen, fluorine, chlorine, or methyl; or is hydrogen or fluorine.

Each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$; or is independently hydrogen, chlorine, fluorine, cyano, methyl, ethyl, $CF_3$, methoxy, ethoxy, $OCF_3$, $CO_2CH_3$, $CH_2CO_2CH_3$, $(CH_2)_{1-4}OCH_3$, or $(CH_2)_{1-4}OCF_3$; or is independently hydrogen, fluorine, chlorine, or methyl; or is hydrogen or fluorine.

$R^a$ and $R^b$ are each independently hydrogen, $C_1$–$C_4$ alkyl, or $(CH_2)_{0-4}OCF_3$; or are each independently hydrogen, methyl, or ethyl; or are each independently hydrogen or methyl; or are both hydrogen.

$R^c$ is hydrogen, $C_1$–$C_4$ alkyl, or $(CH_2)_{0-4}CF_3$; or is hydrogen, methyl, or ethyl; or is hydrogen.

$R^d$ is hydrogen, $C_1$–$C_4$ alkyl, or $(CH_2)_{0-4}CF_3$; or is hydrogen, methyl, ethyl, or $CF_3$; or is hydrogen.

m is an integer from 1 to 3; or is 2 or 3; or is 2.

p and q are each integers from 0 to 3, provided that the sum of p+q is an integer less than or equal to 3. In another embodiment p and q are each independently integers from 0 to 1. In still another embodiment p and q are both 1.

s1 is an integer from 0 to 3; or from 0 to 2; or is 0 or 1.
s2 is an integer from 0 to 3; or from 0 to 2; or is 0 or 1.
s3 is an integer from 0 to 3; or from 0 to 2; or is 0 or 1.
t is an integer from 0 to 2; or is 0 or 1; or is zero.

It is understood that the foregoing embodiments are subject to and are to be read together with the provisos, set forth elsewhere, concerned with compounds having certain Q groups (i.e., q2, q6, or q7). These provisos are controlling, and thus can restrict or exclude one or more of the embodiments, as applied to compounds embraced by these Q groups.

The compounds of the present invention typically exhibit selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while displaying lower affinity for the human alpha 1d and alpha 1b adrenergic receptor subtypes, and many other G-protein coupled human receptors. A class of the compounds of this invention exhibit nanomolar and subnanomolar affinity for the human alpha 1a adrenergic receptor subtype while displaying at least about 10 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). In a subclass of the preceding class, the compounds of this invention exhibit nanomolar and subnanomolar affinity for the human alpha 1a adrenergic receptor subtype while displaying at least about 30-fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors). In another subclass of the preceding class, the compounds of this invention exhibit nanomolar and subnanomolar affinity for the human alpha 1a adrenergic receptor subtype while displaying at least about 100-fold lower affinity for the human alpha 1d and alpha 1b adrenergic receptor subtypes, in addition to exhibiting selectivity over other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intraocular pressure, control of cardiac arrhythrnias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

When compounds according to the invention have at least one chiral center, they may accordingly exist as enantiomers or as mixtures of enantiomers (e.g., racemic mixtures). Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which exhibits selectivity (e.g., at least about ten fold selectivity) for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g., PCT International Application Publication No. WO94/10989, published May 26, 1994; U.S. Pat. No. 5403847, issued Apr. 4, 1995]. Compounds which are both selective amongst the various human alpha 1 adrenergic receptor subtypes and which have low affinity for other receptors, such as the alpha 2 adrenergic receptors, the B-adrenergic receptors, the muscarinic receptors, the serotonin receptors, the histamine receptors, and others are particularly preferred. The absence of these non-specific activities may be confirmed by using cloned and expressed receptors in an analogous fashion to the method disclosed herein for identifying compounds which have high affinity for the various human alpha 1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin. Other dispersing agents which may be employed include glycerin and the like.

For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. No. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as Sa-reductase inhibitors have been described in WO 93/23420, EP 0572166; WO 93/23050; WO 93/23038; WO 93/23048; WO 93/23041; WO 93/23040; WO 93/23039; WO 93/23376; WO 93/23419, EP 0572165; WO 93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. Nos. 4,377,584 and 4,760,071 which describe dosages and formulations for 5a-reductase inhibitors.

Abbreviations used in the instant specification, particularly the chemes and Examples, are as follows:

Boc or BOC=t-butyloxycarbonyl
DMF=N,N-dimethylformamide
DMSO=dimethyl sulfoxide
EDTA=ethylenediamine tetraacetic acid
Et=ethyl
EtOAc=ethyl acetate
Et$_3$N=triethylamine
FAB-MS=fast atom bombardment mass spectroscopy
HPLC=high performance liquid chromatography
Me=methyl
m.p.=melting point
p-MeOBzBr=p-methoxybenzylbromide
Ph=phenyl
Pr=propyl
TFA=trifluoroacetic acid
THF=tetrahydrofuran The compounds of the present invention can be readily prepared according to the following reaction schemes and examples, or modifications thereof, using readily available starting materials, reagents and conventional synthetic procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be prepared via Schemes 1 and 2 shown below. Scheme 1 describes the preparation of compounds of Formula (I) in which the substituent on the N-1 nitrogen in the hydantoin ring is hydrogen (i.e., $R^6$=H). In Scheme 1a suitable arylhydantoin (i.e., 5-arylimidazolidine-2,4-dione) precursor is prepared by reacting the corresponding aryl ketone with KCN and ammonium carbonate in the presence of wet DMF. Further description of this and other methods for preparing suitable arylhydantoin precursors can be found in Ware, *Chem. Rev.* 1950, 46: 403–457. The arylhydantoin precursor can then be alkylated at the N-3 nitrogen with a suitable dihaloalkane (e.g. 1,3-dibromopropane) to obtain a 3-haloalkyl spiroimidazolidinedione intermediate, which can then be aminated by heating with amine Q—H in dry DMF and triethylamine to provide the compound of the invention.

Scheme 2 describes the preparation of compounds identical to those of Scheme 1, except that the N-1 nitrogen of the hydantoin ring has a substituent other than H (i.e., $R^6$ is other than hydrogen). This scheme is similar to Scheme 1, except that the N-3 nitrogen on the hydantoin ring (the more reactive nitrogen) is first protected with a removable protecting group such as p-methoxybenzyl, then the $R^6$ group is introduced (e.g., alkylating with an alkyl bromide to introduce an alkyl group). The protecting group can then be removed with ceric ammonium nitrate in aqueous acetonitrile and the N-3 nitrogen can be alkylated and then aminated as in Scheme 1. Alternatively, compounds of the invention with $R^6$ being other than hydrogen can be prepared by direct alkylation of a compound of the invention prepared as in Scheme 1 (i.e., having $R^6$=H) with a suitable alkylating agent and using NaH in DMF to deprotonate the hydantoin. Suitable alkylating agents include alkyl haloacetates (e.g., ethyl bromoacetate), haloalkyl ethers (e.g., chloromethyl methyl ether or chloromethyl ethyl ether), alkyl halides (e.g., methyl bromide), and haloacetamides. Still other approaches which can be utilized involve incorporation of the desired compatible substituted nitrogen during a stepwise construction of the hydantoin ring, as described generally in Ware, *Chem. Rev.* 1950, 46: 403–457.

SCHEME 1

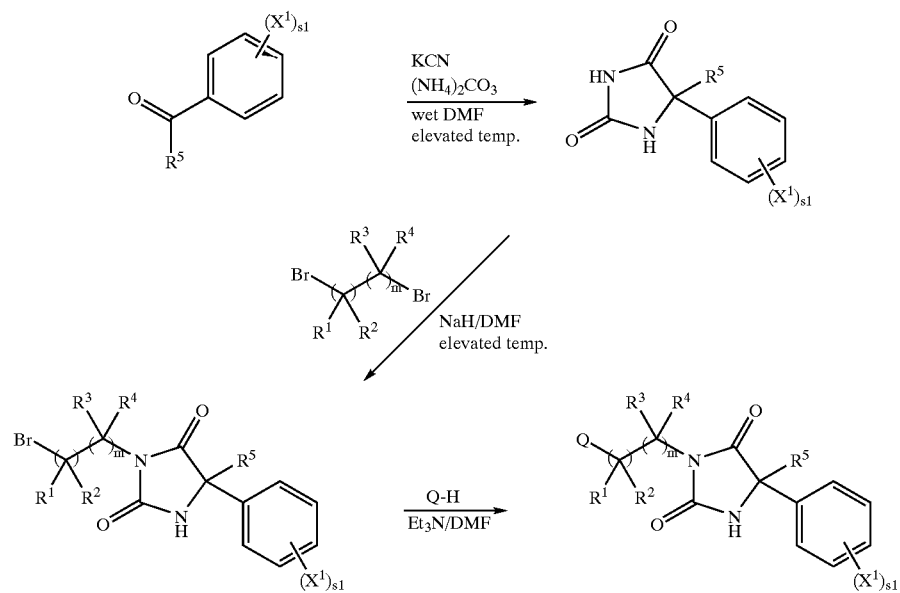

SCHEME 2

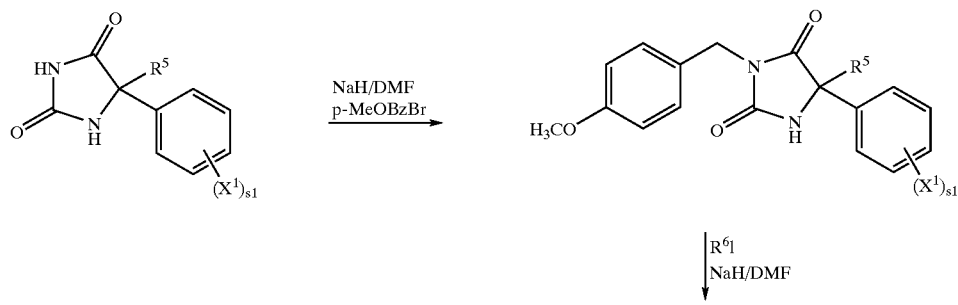

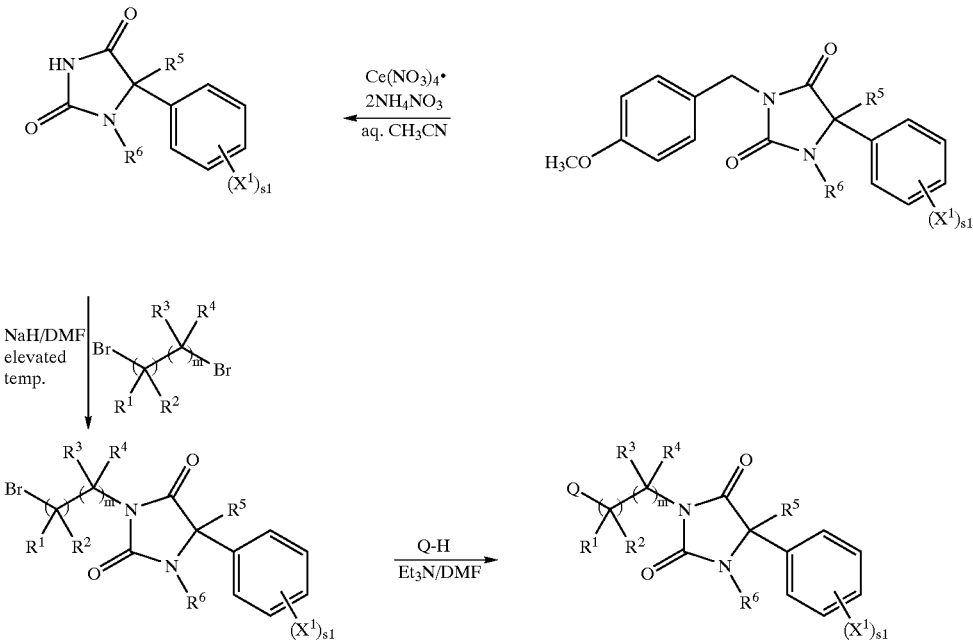

The amines of formula Q—H which are coupled to the arylhydantoin intermediates to obtain compounds of the invention can be prepared using procedures the same or similar to those known in the art. Thus, for example, amines Q—H with Q of formula q1 can be prepared as illustrated in Scheme 3 for aryl- and heteroaryl-piperidines. In accordance with Scheme 3-A, 1-Boc-4-piperidone can be reacted with LDA and n-phenyltrifluoromethane sulfonimide to provide the 1,2,5,6-tetrahydropyridin- 4-yl ester of trifluoromethane sulfonic acid which, upon reaction with aryl zinc iodide in the presence of tetrakis (triphenylphosphine) palladium will provide 1-Boc-4-aryl-1,2,5,6-tetrahydropyridine which is hydrogenated to 1-Boc-4-arylpiperidine, followed by deprotection (e.g., by reaction with HCl) to obtain the piperidine. Scheme 3-B is a variation of 3-A in which 4-aryl-4-hydroxypiperidin-1-yl substituents can be obtained. In accordance with 3-B, an arylmagnesium bromide can be reacted with 1-Boc-4-piperidone to obtain 1-Boc4-aryl4-hydroxy piperidine which can be deprotected (e.g., by reation with HCl). Scheme 3-C provides a general method for preparing 4-aryl-4-cyanopiperidines. Arylacetonitrile accordingly can be reacted with bis-2-chloroethyl-tert-butoxycarbonylamine and NaH or cesium carbonate to provide 1-Boc-4-aryl-4-cyano-piperidine, which can be deprotected by conventional procedures (e.g., by reaction with HCl.)

Further description of the preparation of suitable amines Q—H with Q=q1 can be found in U.S. Pat. No. 5,661,163 and in WO 96/19967.

Amines Q—H with Q of formula q2 (i.e., piperazines) can be prepared in accordance with procedures the same or sinilar to those described in WO 97/17967. Further guidance on the preparation of piperazines suitable for use in making compounds of the present invention can be found in G. B. Barlin, The Pyrazines, Wiley Interscience, 1982, 372–376 and in Heterocyclic Compounds, vol. 6, edited by Robert C. Elderfield, John Wiley, 1957, 423–430.

Amines Q—H with Q of formula q3 can be prepared by the reductive amination between suitable amines and protected piperidones, as illustrated in Scheme 4.

Many amines Q—H with Q of formula q4 and q6 can be prepared by the methods set forth in Schemes 5–10 below. Scheme 5 shows the preparation of spiroindanyl- and spiroindenyl-piperidines, wherein indene L1 is reacted with a strong base (e.g., LHMDA, LDA, or sodium or potassium hydride) and then with N-Boc-bis-(2-chloroethyl)amine to form the Boc-protected spiroindene piperidine L2, which is treated with acid (e.g., TFA in $CH_2Cl_2$ or HCl in cold EtOAc) to obtain spiro[1H-indeno-1,4'-piperidine] L3. Reduction of L2 ($H_2$ and palladium on carbon catalyst) followed by nitrogen deprotection (or, alternatively, reduction of L3) affords the spiro[indano-1,4'-piperidine] L4. For further description of this chemistry, see *J. Med. Chem.* 1992, 35: 2033–2039 and 3919–3927.

Other N-Boc-bis-(haloalkyl)amines can be used in place of N-Boc-bis(2-chloroethyl)amine to provide a wide range of spiroindene and spiroindane azacycloalkanes suitable for preparing compounds of the invention; i.e., Boc-protected amines of formula:

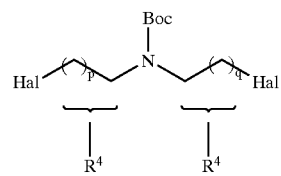

can be used to obtain spirocyclic amines of formula:

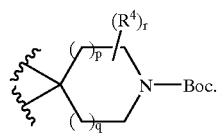

Scheme 6 provides a method for forming spiro[indano-1,4'-piperidin]-2-ones, wherein Boc-protected spiroindene piperidine L5 is treated with a peroxy acid to obtain epoxide intermediate L6, which forms the corresponding spiroindan- 2-one L7 upon treatment with a Lewis acid. Nitrogen deprotection by treatment with an acid such as TFA provides L8. Alternatively, L7 can be alkylated on the indanone ring by reaction with alkyl halide and then nitrogen deprotected to afford L9.

Scheme 7 shows a method for forming spiro [benzocycloalkane-2,4'-piperidin]-1-ones via chemistry previously described in Scheme 8. Further description of this chemistry can be found in Biorg. Med. Chem. Lett. 1998, 8: 107–112. As noted above in discussing Scheme 5, other N-Boc-bis-(haloalkyl)amines can be used in place of N-Boc-bis(2-chloroethyl)amine in this scheme to provide a wide range of spiroindan-1-one azacycloalkanes suitable for preparing compounds of the invention.

Scheme 8 shows a method for forming spiro [isobenzofuran-1(3H),4'-piperidines] and spiro [isobenzofuran-1(3H),4'-piperidin]-3-ones. N-phenylbenzamide L13 is lithiated with n-butyllithium and then reacted with N-Boc-piperidone to afford -Boc-spiro [isobenzofuran-1(3H),4'-piperidin]-3-one L14, which can be treated with acid to form the deprotected analog L15. Alternatively, L14 can be reduced with borane and then deprotected to provide spiro[isobenzofuran-1(3H),4'-piperidine] L16. Further description of this chemistry can be found in *J. Org. Chem.* 1975, 40: 1427–1433.

Scheme 9 shows a method for forming spiro[3H-indole-3,4'-piperidin]-2(1H)-ones, in which 3H-indol-2(1H)-one L17 is treated with a strong base (e.g., LHMDA, LDA, or sodium or potassium hydride) and then with N-Boc-bis-(2-chloroethyl)amine to form the Boc-protected spiroindolyl piperidine L18, which is treated with acid (e.g., TFA in $CH_2Cl_2$ or HCl in cold EtOAc) to obtain L19. Further description of this chemistry can be found in *Org. Prep. Proced. Int.* 1995, 27: 691–694. [Note: This reference teaches that the first step of Scheme 8 works with a benzyl-protected reagent, but not with a Boc-protected reagent. Boc-protected reagents have been found herein to work satisfactorily with a suitable choice of strong base.] As noted above in discussing Schemes 5 and 7, other N-Boc-bis-(haloalkyl)amines can be used in place of N-Boc-bis(2-chloroethyl)amine in this scheme to provide a variety of analogs of L19.

Scheme 10 shows a method for forming spiro[4H-3,1-benzoxazine-4,4'-piperidine]-2(1H)-ones. Halo-substituted aniline L20 is treated with di-t-butylcarbonate to obtain L21, which is lithiated with t-butyllithium and reacted with a Boc'ed piperidone to obtain Boc-protected halobenzoxazinone L22, which can be deprotected by treatment with an acid to form L24, or can be N-alkylated on the benzoxazine ring by treatment with an alkyl halide and then deprotected to form L25. Alternatively, L22 can be dehalogneated by treatment with $H_2$/Pd to obtain L23, which can then be nitrogen-deprotected to afford L26, or can be N-alkylated and deprotected to form L27. Further description of this chemistry can be found in *J. Med. Chem.* 1983, 26: 657–661, *Chem. Pharm. Bull.* 1985, 33: 1129–1139, and U.S. Pat. No. 4,349,549.

Methods for preparing a variety of 1,2-dihydro-spiro[3H-indole-3,4'-piperidines] are disclosed in U.S. Pat. No. 5,536, 716. For example, the preparations of 1,2-dihydro-1-methanesulfonylspiro[3H-indole-3,4'-piperidine] and spiro [3H-indole-3,4'-piperidine] are respectively described in Example 18, Step A and in Example 21, Step A.

Amines Q—H with Q of formula q5 can be prepared by reductive amination of spirobicyclic cycloalkanones with suitable amines, as shown in Scheme 11.

Amines Q—H with Q of formula q7 can be prepared in accordance with procedures described in WO 96/25934.

SCHEME 3

A.

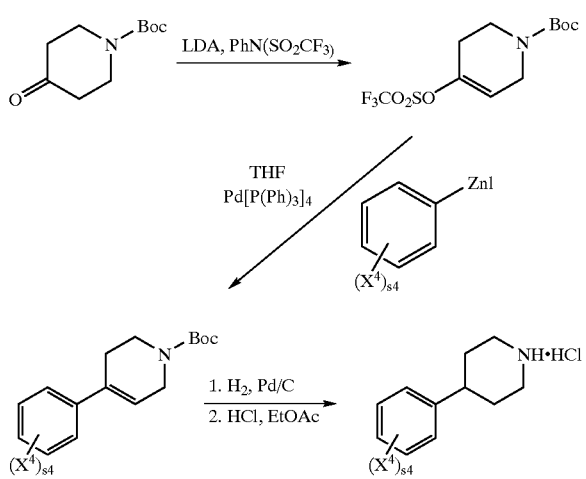

B.

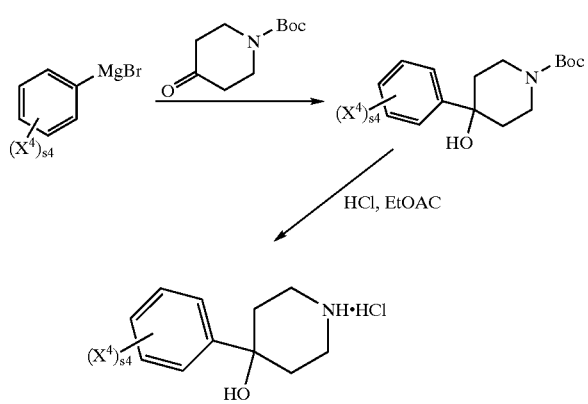

C.

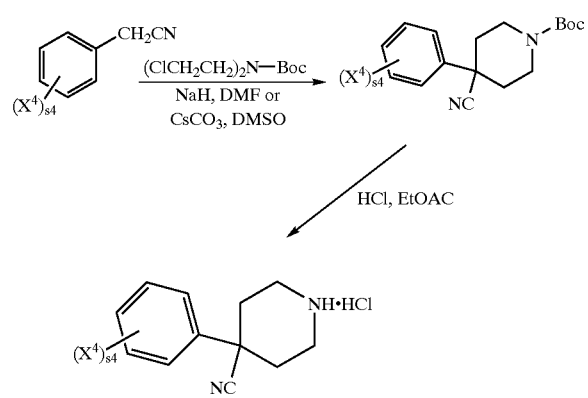

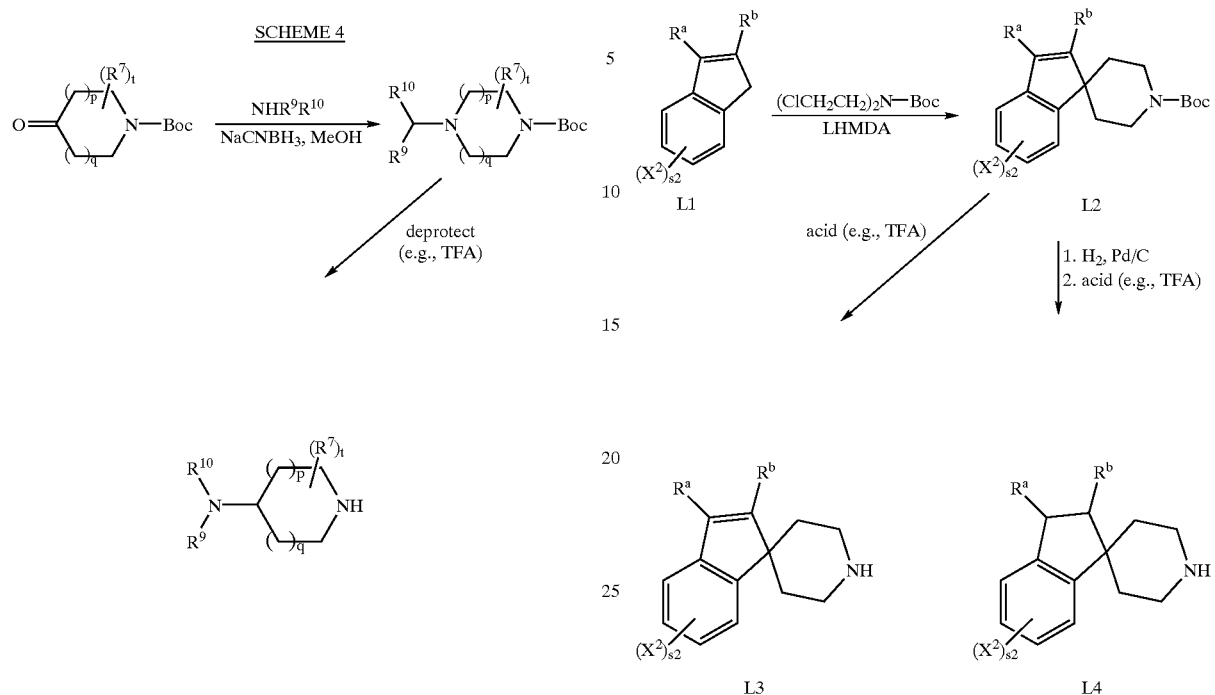

-continued
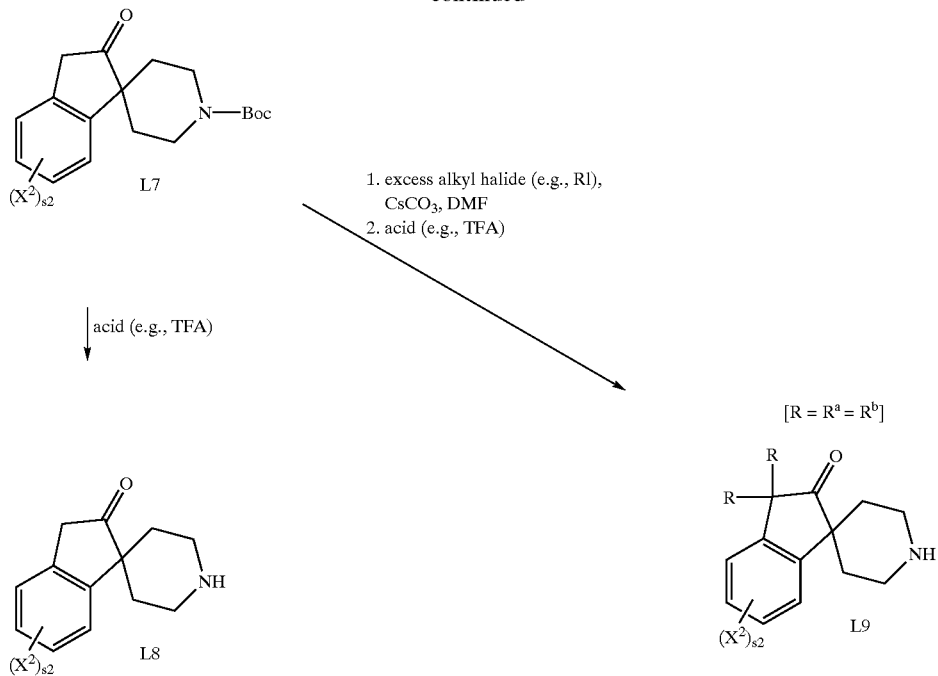
SCHEME 7
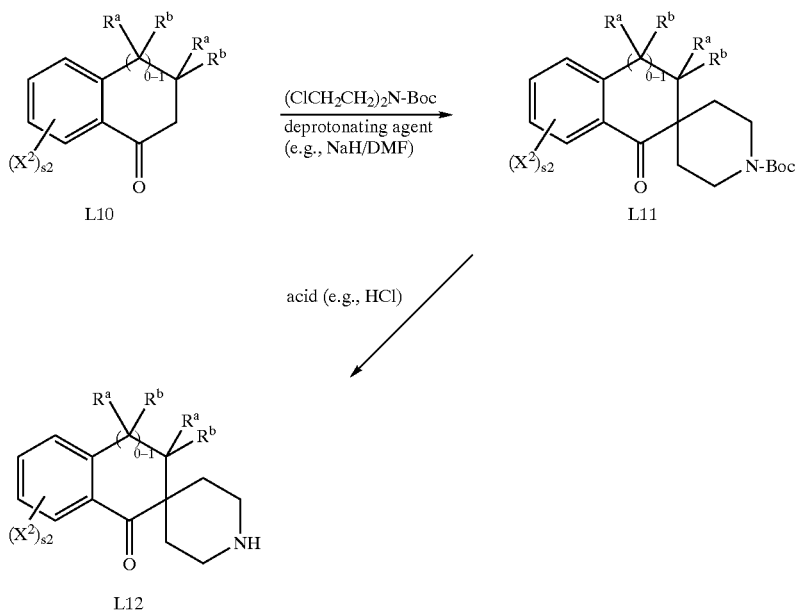

SCHEME 8
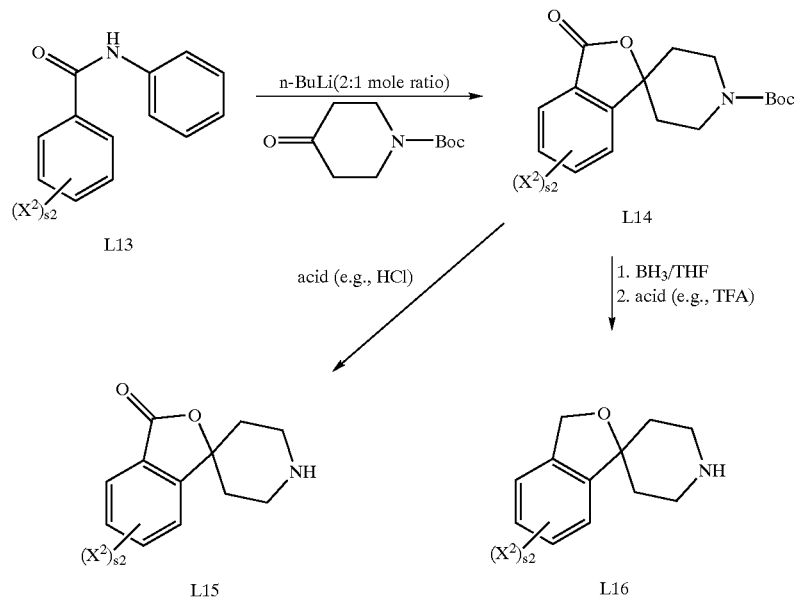
SCHEME 9
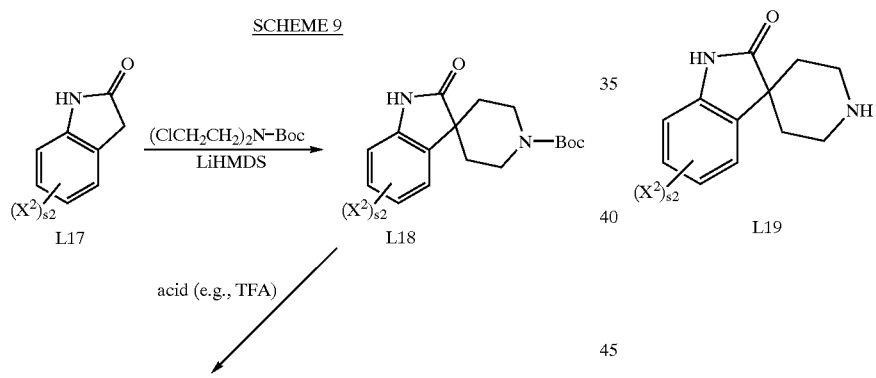
-continued
SCHEME 10
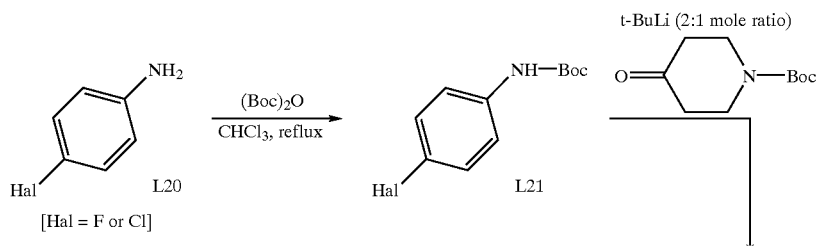
[Hal = F or Cl]

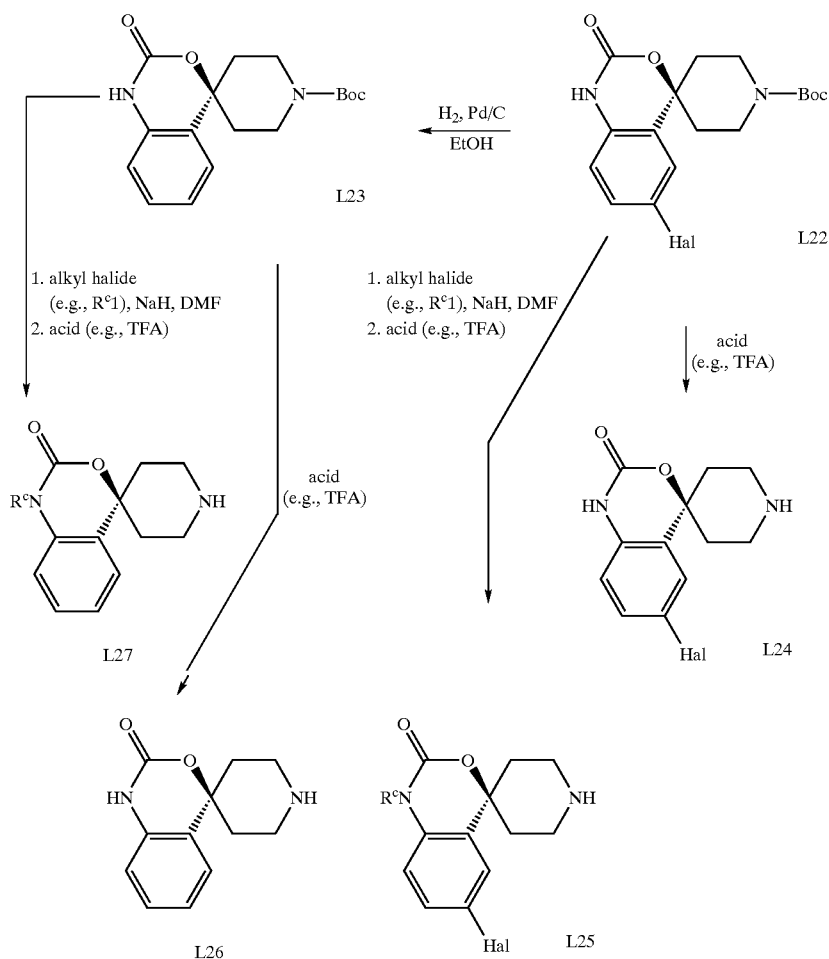

SCHEME 11

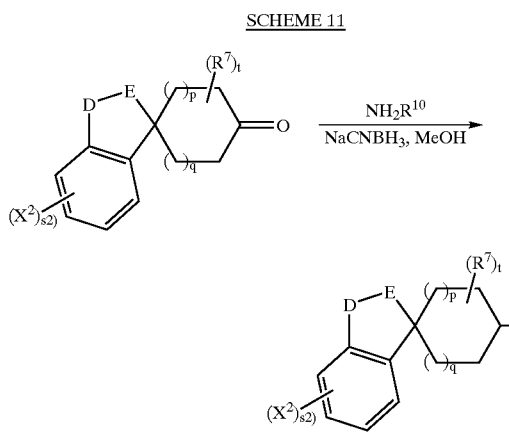

The following examples serve only to illustrate the invention and its practice. The examples are not to be construed as limitations on the scope or spirit of the invention.

Example 1

3-[3-(4-Phenyl-4-cyanopiperidin-1-yl)propyl]-5,5-bis(4-methylphenyl)-imidazolin-2,4-dione (1)

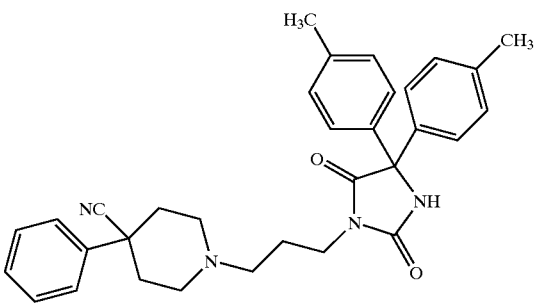

Step A: Preparation of bis-5,5-(4-methylphenyl)-imidazolin-2,4-dione

A solution of bis(4-methylphenyl)ketone (1.05 gm., 5.0 mmol) in dimethylformamide (10 mL) and water (0.5 mL) containing potassium cyanide (405 mg., 6.2 mmol) and ammonium carbonate(1.6 gm., 16.7 mmol) was sealed in a screw-top glass tubular vessel and heated at 130° C. for 24 hours. The cooled reaction vessel was opened and the contents poured into water and acidified with conc. HCl. The resulting precipitate was collected by filtration rinsed with water and dried. This solid was digested in ethyl acetate to give purified product. m.p.: >260° C.

Step B: Preparation of 3-bromopropyl-5,5-bis(4-methylphenyl)-imidazolin-2,4-dione Bis-5,5-(4-methylphenyl)-imidazolin-2,4-dione (560 mg, 2.0 mmol) was dissolved in dry dimethylforarnide (6 mL) and 60% sodium hydride in mineral oil (99 mg, 2.5 mmol) was added. The mixture was warmed at 50° C. for 10 minutes to give a thick precipitate and then 1,3-dibromopropane (1.1 mL, 10.9 mmol) was added. The reaction mixture was warmed at 50° C. for 3 hours. The cooled reaction mixture was diluted with ethyl acetate and the organic solution was washed with aq. NaHCO3 and water (3×). The dried extract was evaporated and chromatographed on silica gel using a 10–30% ethyl acetate/hexane gradient. The appropriate fractions were combined and evaporated and the residue was triturated with hexane/ether to give the product as a white solid. m.p.: 105–106° C.

Step C: Preparation of 3-[3-(4-Phenyl-4-cyanopiperidin-1-yl)propyl]-5,5-bis(4-methylphenyl)-imidazolin-2,4-dione (1)

A solution of 4-phenyl-4-cyanopiperidine (328 mg, 1.76 mmol) and 3-bromopropyl-5,5-bis(4-methylphenyl)-imidazolin-2,4-dione (603 mg, 1.5 mmol) in dry dimethylformamide (3 mL) containing triethyl amine (0.28 mL, 2.0 mmol) was warmed at 50° C. for four hours. The cooled reaction mixture was diluted with ethyl acetate. This solution was washed with aq. Na2CO3, water (3×), and then dried over anhydrous Na2SO4, filtered through a pad of charcoal and the solvent evaporated. The residue was triturated with methanol to give pure crystalline product. m.p.: 157–159° C.

Analysis calculated for C32H34N4O2: C, 75.86; H, 6.76; N, 11.06. Found: C, 75.95; H, 6.79; N, 10.97.

EXAMPLE 2

The following compounds were prepared in accordance with the procedures set forth in Example 1, Step C, except that the appropriate piperidine (listed below) was employed instead of 4-phenyl-4-cyanopiperidine.

3-{3-[4-(2-Methylphenyl)-4-cyanopiperidin-1-yl]propyl}-5,5-bis(4-methylphenyl)-imidazolin-2,4-dione (2)

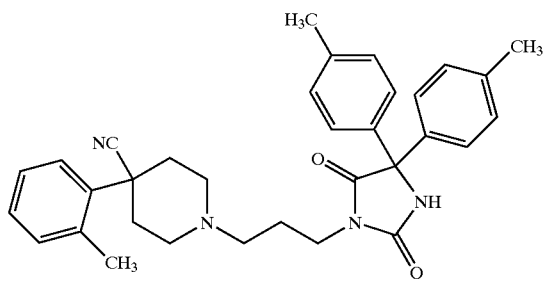

piperidine: 4-(2-methylphenyl)-4-cyanopiperidine
m.p.: 164–165° C.

Analysis calculated for C33H36N4O2.0.3 C4H8O2(ethyl acetate): C, 75.07; H, 7.07; N, 10.24. Found: C, 74.73; H, 6.91; N, 10.56.

3-{3-[4-(2-Pyridyl)piperidin-1-yl]propyl}-5,5-bis(4-methylphenyl)-imidazolin-2,4-dione (3)

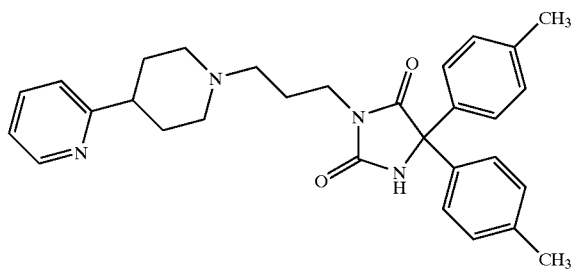

piperidine: 4-(2-pyridyl)piperidine
m.p.: 164–167° C.

Analysis calculated for C30H34N4O2.0.3 C4H8O2(ethyl acetate) C, 73.61; H, 7.21; N, 11.01. Found: C, 73.49; H, 7.16; N, 11.02.

3-{3-(spiro[1H-indeno-1,4'-piperidin]-1'-yl)propyl}-5,5-bis(4-methylphenyl)-imidazolin-2,4-dione (4)

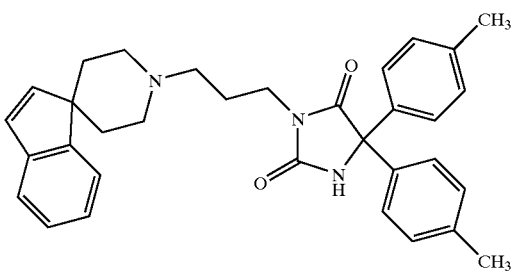

piperidine: spiro-(1H-indeno-1,4'-piperidine)
m.p.: 173–175° C.

Analysis calculated for C33H35N3O2.0.3 C4H10O (diethyl ether): C, 77.81; H, 7.26; N, 7.96. Found: C, 77.85; H, 7.26; N, 7.78.

3-{3-(2,3-dihydro-spiro[indeno-1,4'-piperidin]-2(3H)-on-1'-yl)propyl}-5,5-bis(4-methylphenyl)-imidazolin-2,4-dione (5)

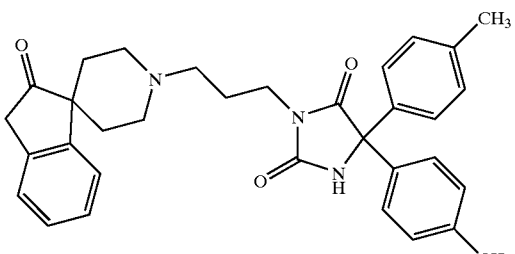

piperidine: spiro[inden-2(3H)-one-1,4'-piperidine]
m.p.: 188–195° C.

Analysis calculated for C33H35N3O2.0.1 C4H10O (diethyl ether).0.2 H2O: C, 75.30; H, 6.89; N, 7.89. Found: C, 75.28; H, 6.91; N, 7.87.

3-{3-(spiro[4H-3,1-benzoxazine-4,4'-piperidin]-2 (1H)-on-1'-yl)propyl}-5,5-bis(4-methylphenyl)-imidazolin-2,4-dione (6)

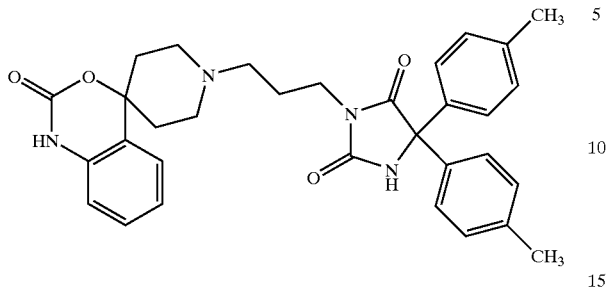

piperidine: spiro[4H-3,1-benzoxazin-2(1H)one-4,4'-piperidine]

Analysis calculated for C32H34N4O4.0.3 C4H10O (diethyl ether).0.5 H2O: C, 69.97; H, 6.72; N, 9.83. Found: C, 69.99; H, 6.61; N, 9.83.

3-{3-(6-chloro-spiro[4H-3,1-benzoxazine-4,4'-piperidin]-2(1H)-on-1'-yl )propyl}-5,5-bis(4-methylphenyl)-imidazolin-2,4-dione (7)

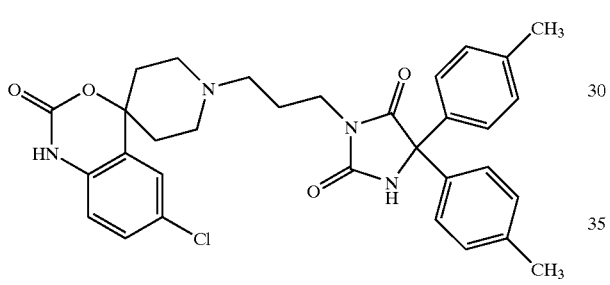

piperidine: 6-chloro-spiro[4H-3,1-benzoxazin-2(1H)one-4,4'-piperidine]

m.p.: 235–240° C.

Analysis calculated for C32H33ClN4O4.1.45 H2O: C, 64.14; H, 6.04; N, 9.35. Found: C, 64.13; H, 5.70; N, 9.29.

3-{3-(1-methyl-6-chloro-spiro[4H-3,1-benzoxazine-4,4'-piperidin]-2(1H)-on-1'yl)propyl}5,5-bis(4-methylphenyl)-imidazolin-2,4-dione (8)

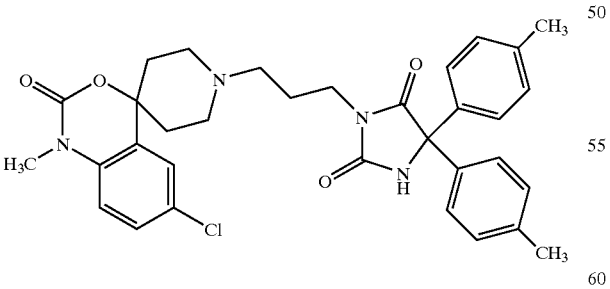

piperidine: 1-methyl-6-chloro-spiro[4H-3,1-benzoxazin-2(1H)one-4,4'-piperidine]

m.p.: 99–106° C.

Analysis calculated for C33H35ClN4O4.0.45 H2O: C, 66.58; H, 6.08; N, 9.41. Found: C, 66.58; H, 6.47; N, 9.59.

3-{(3-(1-methyl-spiro[4H-3,1-benzoxazine-4,4'-piperidin]-2(1H)-on-1'-yl)propyl}-5,5-bis(4-methylphenyl)-imidazolin-2,4-dione (9)

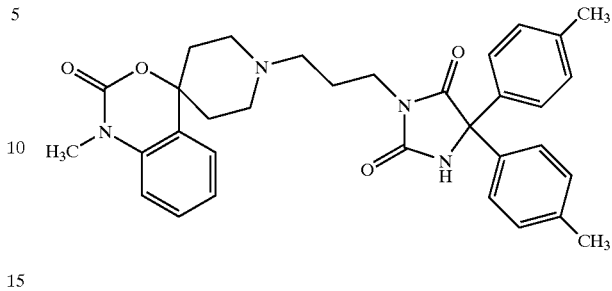

piperidine: 1-methyl-spiro[4H-3,1-benzoxazin-2(1H)one-4,4'-piperidine]

Analysis calculated for C33H36N4O4.0.25 CH2Cl2 (methylene chloride).0.45 H2O: C, 69.04; H, 6.45; N, 9.69. Found: C, 69.08; H, 6.45; N, 9.69.

EXAMPLE 3

The following compounds were prepared in accordance with the procedures set forth in Example 1, except that the appropriate ketone (listed below) was employed instead of bis-(4-methylphenyl)ketone and, if required, the appropriate piperidine (listed below) was employed instead of 4-phenyl-4-cyanopiperidine.

3-{3-[4-phenyl-4-cyanopiperidin-1-yl]propyl}-5,5-bis(4-chlorophenyl)-imidazolin-2,4-dione hydrochloride (10)

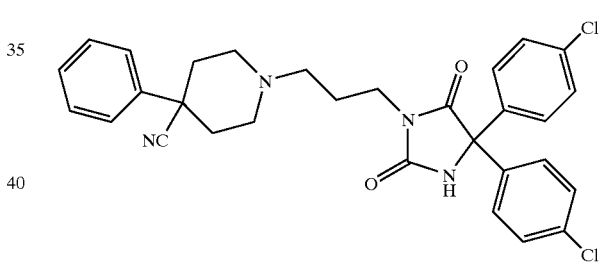

ketone: bis-(4-chlorophenyl)ketone m.p.: 223–225° C.

Analysis calculated for C30H28Cl2N4O2. HCl. 0.6 H2O: C, 60.58; H, 5.12; N, 9.42. Found: C, 60.54; H, 4.96; N, 9.29.

(+/−)-3-{3-[4-phenyl4-cyanopiperidin-1-yl]propyl-}5-(4-methylphenyl)-5-phenyl-imidazolin-2,4-dione trifluoroacetate (11)

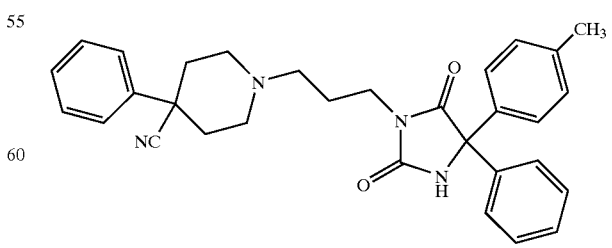

ketone: 4-methylphenyl phenyl ketone m.p.: 179–181° C.

Analysis calculated for C30H28Cl2N4O2. C2HF3O2 (trifluoroacetic acid): C, 65.33; H, 5.48; N, 9.24. Found: C, 64.93; H, 5.46; N, 9.37.

3-{3-[4-(2-methylphenyl)-4-cyanopiperidin-1-yl] propyl}-5,5-bis(4-fluorophenyl)-imidazolin-2,4-dione hydrochloride (12)

piperidine: 4-(2-methylphenyl)-4-cyanopiperidine
ketone: bis-(4-fluorophenyl)ketone
Analysis calculated for C31H30N4O2.HCl.0.70 H2O: C, 64.64; H, 5.65; N, 9.70. Found: C, 64.46; H, 5.53; N, 9.74.

(+/−)-3-{3-[4-(2-methylphenyl)-4-cyanopiperidin-1-yl]propyl}-5-(4-methylphenyl)-5-(2-pyridyl)-imidazolin-2,4-dione (13)

piperidine: 4-(2-methylphenyl)-4-cyanopiperidine
ketone: 4-methylphenyl 2-pyridyl ketone
m.p.: 179–181° C.
Analysis calculated for C31H33N5O2. .0.65 C4H10O (diethyl ethyl).0.55 H2O: C,70.21; H, 6.89; N, 12.18. Found: C,70.20; H, 6.69; N, 12.21.

3-{3-(1-methyl-6- chloro-spiro[4H-3,1-benzoxazine-4,4'-piperidin]-2(1H)-on-1'-yl)propyl}1-5,5-bis(4-chlorophenyl)-imidazolin-2,4-dione (14)

piperidine: 1-methyl-6-chloro-spiro[4H-3,1-benzoxazin-2(1H)one-4,4'-piperidine]
ketone: bis-(4-chlorophenyl)ketone
Analysis calculated for C31H29Cl3N4O4: C, 59.29; H, 4.65; N, 8.92. Found: C, 59.18; H, 4.71; N, 8.80.

EXAMPLE 4

The following compounds were prepared in accordance with the procedures set forth in Example 1, except that the appropriate ketone was employed instead of bis-(4-methylphenyl)ketone and, if required, the appropriate piperidine or piperazine was employed instead of 4-phenyl-4-cyanopiperidine.

3-[3-(4-phenyl-4-cyanopiperidin-1-yl)propyl]-5,5-bis(phenyl)-imidazolin-2,4-dione (15)

m.p.: 161–163° C.
Analysis calculated for C30H30N4O2.0.25 H2O: C, 74.58; H, 6.36; N, 11.60. Found: C, 74.62; H, 6.35; N, 11.3.7

(+/−)-3-{3-[4-(2-methylphenyl)-4-cyanopiperidin-1-yl]propyl}-5-pentyl-4-methylphenyl)-imidazolin-2,4-dione (16)

Analysis calculated for C31H40N4O2. 0.75 H2O: C, 72.41; H. 8.14; N, 10.80 Found: C, 72.41; H, 7.93; N, 10.80.
FAB-MS: 501 (m+1)

(+/−)-3-{3-[4-(2-methylphenyl)-4-cyanopiperidin-1-yl]propyl}-5-pentyl-5-(3,4-difluoro-phenyl)-imdazolin-2,4-dione hydrochloride (17)

Analysis calculated for C30H36F2N4O2.HCl.0.70H2O: C, 63.03; H, 6.77; N, 9.80. Found: C, 63.02; H, 6.64; N, 9.55.
FAB-MS: 523 (m+1)

53

3-{3-(2,3-dihydro-spiro[indeno-1,4'-piperidin]-1'yl)propyl}-5,5-bis(4-methylphenyl)-imidazolin-2,4-dione (18)

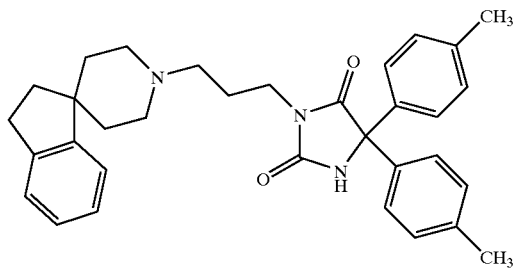

m.p.: 170–172° C.

Analysis calculated for C33H37N3O2. 0.05 C2H2Cl2 (methylene chloride).0.30 H2O: C, 76.73; H, 7.35; N, 8.12. Found: C, 76.53; H, 7.41; N, 8.52.

FAB-MS: 508 (m+1)

3-{4-(2,3-dihydro-spiro[indeno-1,4'-piperidin]-2(3H)-on-1'-yl)butyl}-5,5-bis(4-methylphenyl)-imidazolin-2,4-dione (19)

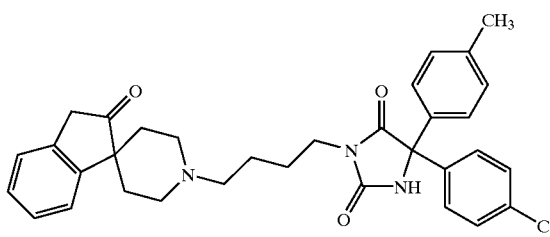

m.p.: 76–88° C.

Analysis calculated for C34H37N3O3.0.25 C4H10O (diethyl ether).0.35 H2O: C, 74.99; H, 7.23; N, 7.50. Found: C, 75.00; H, 7.33; N, 7.52.

FAB-MS: 536 (m+1)

3-{3-(2,3-dihydro-spiro[indeno-2,4'-piperidin]-1(2H)-on-1-yl)propyl}-5,5-bis(4-methylphenyl)-imidazolin-2,4-dione (20)

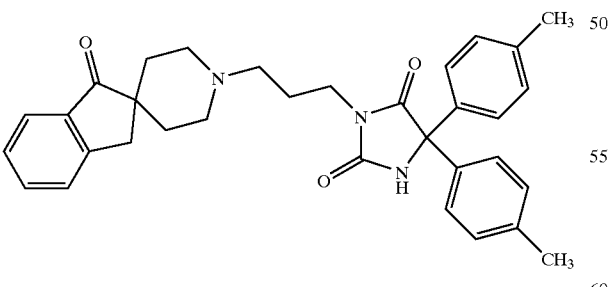

m.p.: 201–205° C.

Analysis calculated for C33H35N3O3.0.30 CH2Cl2 (methylene chloride): C, 73.09; H, 6.56; N, 7.68. Found: C, 73.10; H, 6.59; N, 7.81.

FAB-MS: 522 (m+1)

54

3-{3-(spiro[3H-indole-3,4'-piperidin]-2(1H)-on-1'-yl)propyl}-5,5-bis(4-methylphenyl)-imidazolin-2,4-dione hydrochloride (21)

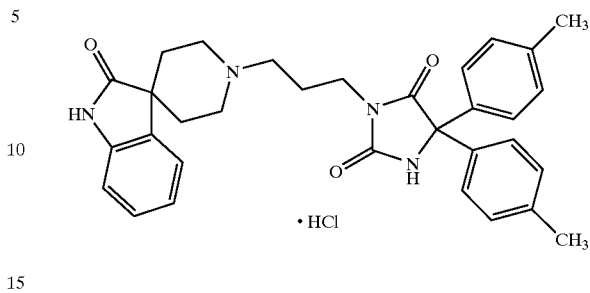

m.p.: >210° C.

Analysis calculated for C32H34N4O3.HCl. 0.65 H2O: C, 67.33; H, 6.41; N, 9.82. Found: C, 67.71; H, 6.36; N, 9.43.

3-{3-(1-methyl-spiro[3H-indole-3,4'piperidin]-2(1H)-on-1'-yl)propyl}-5,5-bis(4-methylphenyl)-imidazolin-2,4-dione (22)

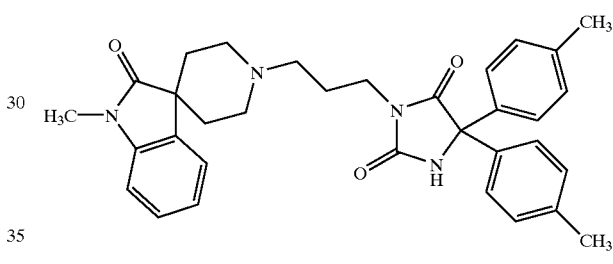

m.p.: 127–135° C.

Analysis calculated for C33H36N4O3.0.75 CH2Cl2 (methylene chloride): C, 67.51; H, 6.30; N, 9.33. Found: C, 67.52; H, 6.20; N, 9.48.

FAB-MS: 537 (m+1)

3-{3-(6-fluoro-spiro[4H-3,1-benzoxazine4,4'-piperidin]-2(1H)-on-1'-yl)propyl}bis(4-methylphenyl)-imidazolin-2,4-dione (23)

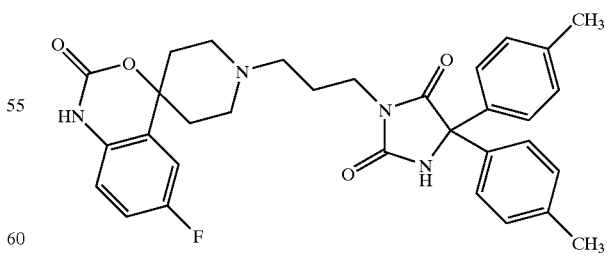

Analysis calculated for C32H33FN4O4: C, 69.05; H, 5.98; N, 10.07. Found: C, 68.81; H, 5.96; N, 9.85.

FAB-MS: 557 (m+1)

3{-3-(4-[4-fluoro-2-(2,2,2-trifluoroethoxy)phenyl]-piperazin-1-yl)propyl}-5,5-bis(4-methylphenyl)-imidazolin-2,4-dione (24)

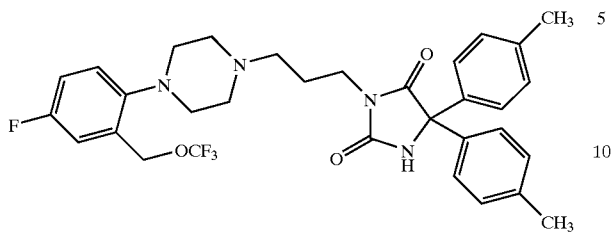

Analysis calculated for C32H34F4N4O3: C, 64.20; H, 5.72; N, 9.36. Found: C, 64.23; H, 5.73; N, 9.46.

3-{3-[4-(2-aminocarbonylphenyl)-piperazin-1-yl]propyl}-5,5-bis(4-methylphenyl)-imidazolin-2,4-dione dihydrochloride (25)

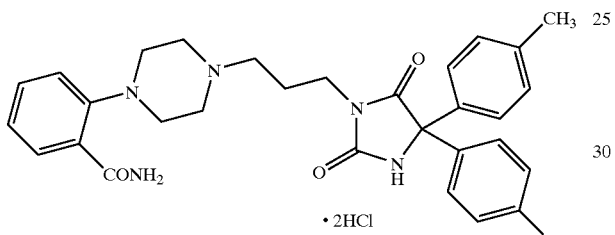

m.p.: 160–163° C.

Analysis calculated for C31H35N5O3.2 HCl. 0.65 H2O: C, 61.01; H, 6.33; N, 11.48. Found: C, 61.01; H, 6.18; N, 11.68.

FAB-MS: 526 (m+1)

(3-{3-[4-(4-fluoro-2-cyanophenyl)piperidin-1-yl]propyl}-5,5-bis(4-methylphenyl)-imidazolin-2,4-dione (26)

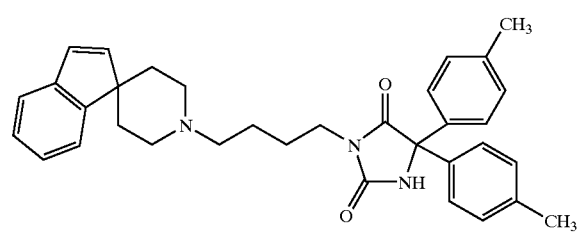

m.p.: 147–149° C.

Analysis calculated for C32H33N4O2: C, 73.26; H, 6.34; N, 10.68. Found: C, 73.35; H, 6.35; N, 10.70.

3-{3-[4-(2-cyanophenyl)-piperazin-1-yl]propyl}-5,5-bis(4-methylphenyl)-imidazolin-2,4-dione hydrochloride (27)

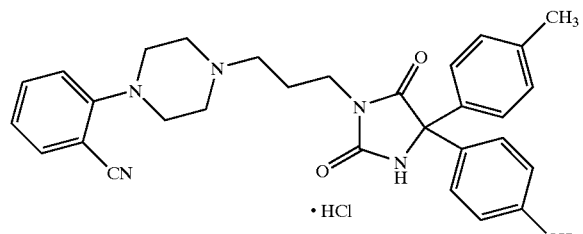

m.p.: 236° C.

Analysis calculated for C31H3N5O3.HCl.0.25 H2O: C, 67.86; H, 6.34; N, 12.77. Found: C, 67.91; H, 6.31; N, 12.46.

FAB-MS: 508 (m+1)

3-{4-(spiro[indeno-1,4'-piperidin]-1'-yl)butyl}-5,5-bis(4-methylphenyl)-imidazolin-2,4-dione (28)

Analysis calculated for C34H37N3O2.1.50 H2O: C, 74.69; H, 7.35; N, 7.69. Found: C, 74.65; H, 7.21; N, 7.51.

FAB-MS: 520 (m+1)

3-{3-[1-(2,2,2-trifluoroethyl)-6-chloro-spiro[4H-3,1-benzoxazine-4,4'-piperidin]-2(1H)-on-1'-yl]propyl}-5,5-bis(4-methylphenyl)-imidazolin-2,4-dione (29)

Analysis calculated for C34H34ClF3N4O4.0.55 H2O: C, 61.40; H, 5.32; N, 8.43. Found: C, 61.38; H, 5.19; N, 8.47.

FAB-MS: 655 (m+1)

(+/−)-3-{3-[4-phenyl-4-cyanopiperidin-1-yl]propyl}-5-methyl-5-phenyl-imidazolin-2,4-dione hydrochloride (30)

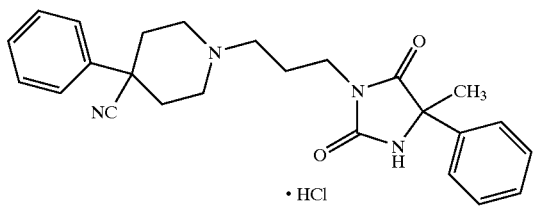

m.p.: 222–223° C.

Analysis calculated for C25H28N4O2.HCl.0.20 H2O: C, 65.76; H, 6.49; N, 12.27. Found: C, 65.74; H, 6.30; N, 11.34.

(+/−)-3-{3-[4-(2-methylphenyl)4-cyanopiperidin-1-yl]propyl}-5-isopropyl-5-(4-methylphenyl)-imidazolin-2,4-dione hydrochloride (31)

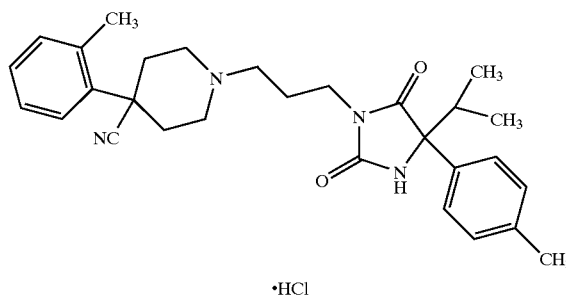

Analysis calculated for C29H36N4O2.0.55 HCl: C, 65.82; H, 7.15; N, 10.59. Found: C, 65.73; H, 7.21; N, 10.41.

FAB-MS: 473 (m+1)

(+/−)-3-{3-[4-(2-methylphenyl)-4-cyanopiperidin-1-yl]propyl}-5-pentyl-5-(4-chlorophenyl)-imidazolin-2,4-dione hydrochloride (32)

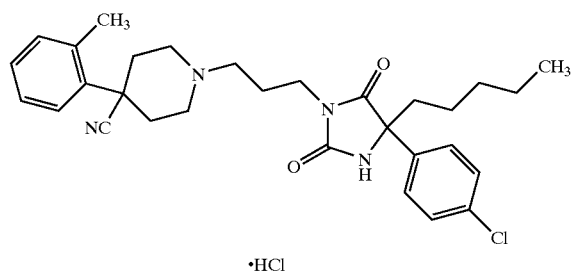

Analysis calculated for C30H36ClN4O2.0.60 HCl: C, 62.29; H, 6.55; N, 9.69. Found: C, 62.34; H, 6.71; N, 9.74.

FAB-MS: 521 (m+1)

(+/−)-3-{-3-[4-(cis-2-chlorophenylamino-3-methoxycarbonylpiperidin-1-yl]propyl}-5,5-bis(4-methylphenyl)-imidazolin-2,4-dione hydrochloride (33)

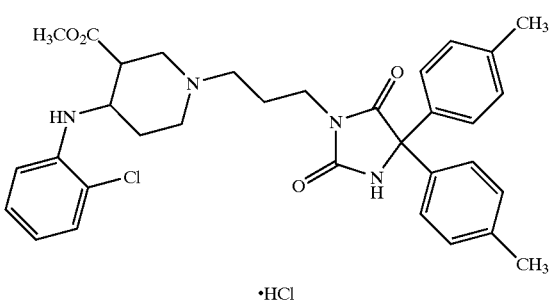

m.p.: 160–163° C.

Analysis calculated for C33H37ClN4O4.HCl.0.55 H2O: C, 62.36; H, 6.20; N, 8.82. Found: C, 62.33; H, 6.21; N, 8.76.

FAB-MS: 589 (m+1)

3-{3-[4-(5-chloro-2-oxo-1-benzimidazolinyl)piperidin-1-yl]propyl}-5,5-bis(4-methylphenyl)-imidazolin-2,4-dione (34)

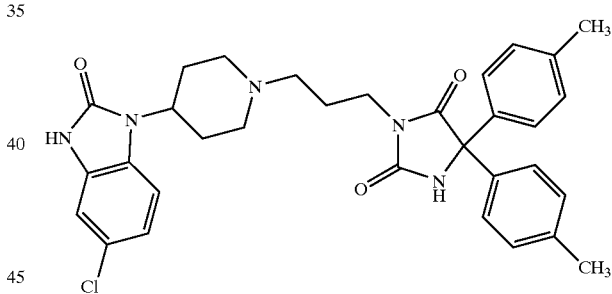

m.p.: 144–155° C.

Analysis calc'd for C32H34ClN5O3.0.10 CH2Cl2 (methylene chloride).0.35 H2O: C, 65.69; H, 5.99; N, 11.93. Found: C, 65.60; H, 6.16; N, 12.28.

FAB-MS: 572 (m+1)

EXAMPLE 5

The following compounds are prepared by direct alkylation of Compound 2 (Example 2) with the appropriate alkylating agent (listed below) using sodium hydride in DMF to deprotonate the hydantoin ring nitrogen.

1-Ethoxycarbonylmethyl-3-{3-[4-(2-methylphenyl)-4-cyanopiperidin-1-yl]propyl}bis-5,5-(4-methylphenyl)-imidazolin-2,4-dione (35)

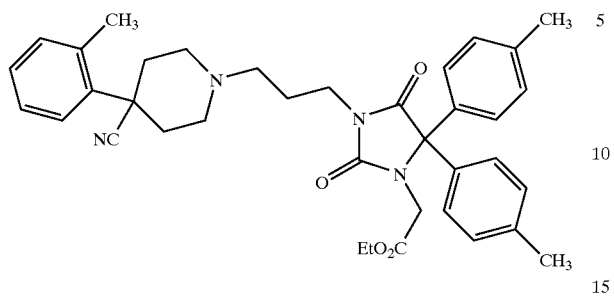

alkylating agent: ethyl bromoacetate
m.p.: 63–65 °C.
Analysis calculated for C37H42N4O4.0.25 CH4O (methanol): C, 72.77; H, 7.05; N, 9.11. Found: C, 72.77; H, 6.93; N, 9.14.
FAB-MS: 607 (m+1)

1-Methyl-3-{3-[4-(2-methylphenyl)-4-cyanopiperidin-1-yl]propyl}-bis-5,5-(4-methylphenyl)-imidazolin-2,4-dione (36)

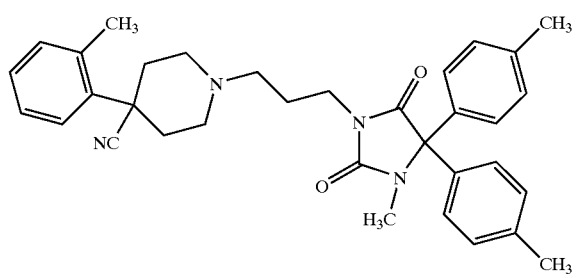

alkylating agent: methyl iodide
Analysis calculated for C34H38N4O2: C, 76.37; H, 7.16; N, 10.48. Found: C, 76.50; H, 7.24; N, 10.40.
FAB-MS: 535 (m+1)

1-methoxymethyl-3-{3-[4-(2-methylphenyl)-4-cyanopiperidin-1-yl]propyl}-5,5-bis(4-methylphenyl)-imidazolin-2,4-dione (37)

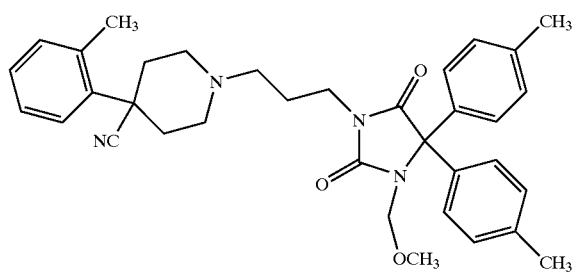

alkylating agent: chloromethyl methyl ether
m.p.: 53–55° C.
Analysis calculated for C35H40N4O3: C, 74.44; H, 7.14; N, 9.92. Found: C, 74.54; H, 7.15; N, 9.65.
FAB-MS: 565 (m+1)

EXAMPLE 6

(+/−)-3-[2-methyl-3-(4-phenyl-4-cyanopiperidin-1-yl)propyl]-5,5-bis(4-methylphenyl)-imidazolin-2,4-dione (38)

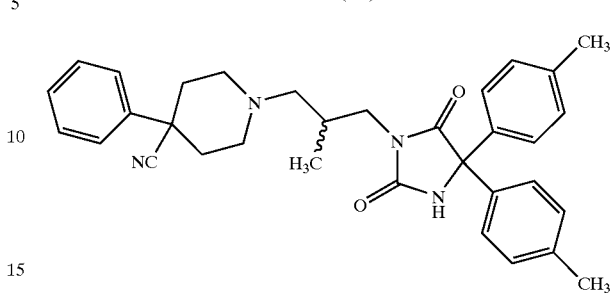

Step A: Preparation of 1-(2-cyanoethyl)-4-cyano-4-phenyl-piperidine

4-Phenyl-4-cyanopiperidine (7 g, 37.6 mmol) and acrylonitrile (2.97 ml, 45.1 mmol) were stirred at room temperature in methanol (34 mL) for 18 hours monitoring the reaction by tlc until complete. The solvent was removed under vacuum and the residue chased with toluene (2x). This residual oil was used directly in the next step Step B: Preparation of (+/−)-1-(2-cyanopropyl)-4-cyano-4-phenyl-piperidine A solution of 1-(2-cyanoethyl)-4-cyano-4-phenyl-piperidine (2.81 g, 11.7 mmol) dissolved in tetrahydrofuran (110 mL) was cooled to −20° C. under an atmosphere of nitrogen and 1 M lithium bistrimethylsilylamide in tetrahydrofuran (12.3 ml) was added by syringe. The clear solution was allowed to stir for 30 min. and then methyl iodide (0.80 mL, 12.9 mmol) was added by syringe. This reaction mixture was stirred for 5 minutes and then warmed to room temperature and stirred for 30 minutes. The reaction was diluted with diethyl ether and washed with water and brine. The organic layer was dried over sodium sulfate, filtered, and the solvent removed to give an oil. This residue was purified by preparative centrifugal chromatography using a 5–50% ethyl acetate/hexane gradient to give the title compound which was used as is.

Step C: Preparation of (+/−)-1-(3-amino-2-methylpropyl)-4-cyano-4-phenyl-piperidine A solution of (+/−)-1-(2-cyanopropyl)-4-cyano-4-phenyl-piperidine (1.75 g, 6.91 mmol) in tetrahydrofuran (12 mL) was cooled to −78° C. and 1 M lithium aluminum hydride in tetrahydrofuran (3.9 ml) was added via syringe. The solution was warmed to −20° C. and after 4.5 hours, the reaction was worked up by sequential addition of water (0.20 mL), 2 M sodium hydroxide (0.40 mL), and water (0.20 mL). The reaction was then warmed to room temperature and diluted with ethyl acetate. The organic layer was washed with aq. sodium hydroxide and brine and dried over sodium sulfate. The filtered organic extract was concentrated to give an oil which was used without further purification.

Step D: Preparation of methyl bis(4-methylphenyl) azidoacetate

Sodium bistrimethylsilylamide (1M solution in tetrahydrofuran, 9.82 ml) was added to a solution of methyl bis(4-methylphenyl)acetate (2.08 g, 8.18 mmol) dissolved in tetrahydrofuran (10 mL) and cooled to −78° C. under a nitrogen atmosphere. The reaction was stirred for 2.5 hours and then a solution of 2,4,6-triisopropylbenzenesulfonyl azide (2.78 g, 9 mmol) in tetrahydrofuran (6 mL) was added. This mixture was stirred for 45 minutes and then warmed to room temperature and stirred for an additional two hours.

Glacial acetic acid (1.5 ml) was added and the mixture was stirred for 30 minutes. The reaction was diluted with diethyl ether and washed with saturated sodium bicarbonate and brine. The organic layer was dried over sodium sulfate, filtered and concentrated to afford crude product. This material was chromatographed on a column of silica gel eluting with 10% ethyl acetate/hexane to give the purified title compound as an oil which was used as is.

Step E: Preparation of bis(4-methylphenyl)azidoacetic acid

To a solution of methyl bis(4-methylphenyl)azidoacetate (2.07 g, 7.01 mmol) in tetrahydrofuran(15 mL) was added 2 M aqueous sodium hydroxide (3.86 ml, 7.71 mmol). The mixture was stirred at room temperature for 18 hours, and then the solvents were removed in vacuo. The residue was dissolved in ethyl acetate and washed with 1M HCl and brine. The organic layer was dried over sodium sulfate, filtered and concentrated to give the title compound as a waxy solid which was used as is.

Step F: Preparation of (+/−)-1-[3-bis(4-methylphenyl) azidoacetamido-2-methyl-propyl]-4-cyano-4-phenyl-piperidine To a solution of (+/−)-1-(3-amino-2-methylpropyl)-4-cyano-4-phenyl-piperidine (735 mg, 1.71 mmol), from Step C, and bis(4-methylphenyl)azidoacetic acid (482 mg, 1.713 mmol), from Step E, in dimethylformamide (4 mL) was added 1-hydroxybenzo-triazole hydrate (255 mg, 1.88 mmol) followed by 1-ethyl-3-(3-dimethylamino-propyl)-carbodiimide hydrochloride (361 mg, 1.88 mmol). The mixture was stirred for 5 min. at room temperature before solid sodium bicarbonate (1.15 g, 13.7 mmol) was added. After stirring for another hour at room temperature, the solvent was removed in vacuo. The residue obtained was taken up in ethyl acetate and washed with water and brine. The organic layer was dried over sodium sulfate, filtered, and concentrated to give the crude product which was purified by preparative centrifugal chromatography using a 1–2% methanol/chloroform gradient. The isolated title compound was used as is.

Step G: Preparation of (+/−)-1-[3-bis(4-methylphenyl) aminoacetamido-2-methyl-propyl]-4-cyano-4-phenyl-piperidine A solution of (+/−)-1-[3-bis(4-methylphenyl) azidoacetamido-2-methyl-propyl]-4-cyano-4-phenyl]-piperidine (300 mg (0.576 mmol) in absolute ethanol (6.5 mL) containing a suspension of 10% palladium on carbon (300 mg) was hydrogenated at atmospheric pressure for 2.5 hours. The reaction was diluted with absolute ethanol and filtered through a pad of celite. The filtrate was concentrated in vacuo, and the residue was chased with toluene to give the crude product which was used without further purification.

Step H: Preparation of (+/−)-3-[2-methyl-3-(4-phenyl-4-cyanopiperidin-1-yl)propyl]-5,5-bis(4-methylphenyl)-imidazolin-2,4-dione A solution of (+/−)-1-(3-bis(4-methylphenyl) aminoacetamido-2-methyl)-propyl-4-cyano-4-phenyl-piperidine (124 mg (0.251 mmol) in tetrahydrofuran(6.3 mL) was cooled to 0° C. and triethylamine (0.05 mL, 0.36 mmol) was added along with of triphosgene ( 24.8 mg, 0.084 mmol). Finally, additional triethylamine (0.05 mL, 0.36 ml) was added, and the mixture was stirred for another 5 minutes. It was then warmed to room temperature and stirred for 18 hours. The tetrahydrofuran was removed in vacuo, and the residue was taken up in ethyl acetate and washed with water and brine. The organic layer was dried over sodium sulfate, filtered and concentrated. This crude product was purified by preparative layer chromatography on 0.5 mm silica gel plates eluting with 3% methanol chloroform to give the title compound as an amorphous solid.

Analysis calculated for C33H36N4O2.0.05 CHCl3.0.60 C4H8O2(ethyl acetate): C, 73.47; H, 7.11; N, 9.67 Found: C, 73.50; H, 6.71; N, 9.40

FAB-MS: 521 (m+1)

EXAMPLE 7

As a specific embodiment of an oral composition, 100 mg of the (+)-enantiomer of Example 1 (i.e., compound 1) is formulated with sufficient finely divided lactose to provide a total amount of 580 to 590 mg to fill a size O hard gel capsule.

EXAMPLE 8

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 9

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$ I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in Examples 1–6 were found to have alpha 1a Ki values of less than about 215 nM, as determined via the screening assay described in Example 8. The following compounds were found to have alpha 1a Ki values of less than about 20 nM: 1–29, 31 and 36.

All of the compounds prepared in Examples 1–6 were found to be at least about 10-fold more selective in binding to the alpha 1a receptors versus binding to the alpha 1b and alpha 1d receptors. The following compounds were found to be at least about 30-fold more selective in binding to alpha 1a receptors versus binding to the alpha 1b and alpha 1d receptors: 1–25, 35 and 36.

The following compounds were found to have alpha 1a Ki values of less than about 10 nM and also found to be at least about 100-fold more selective in binding to the alpha 1a receptors versus binding to the alpha 1b and alpha 1d receptors: 1–9 and 11–14.

EXAMPLE 10

Counterscreen: Histamine-1 Selectivity

The binding affinity (Ki in nM) of the compounds of the present invention for histamine H1 receptors can determined via the binding assay described in Chang et al., *J. Neurochem.* (1979), 32: 1653, or as described in U.S. Pat. No. 5,403,847, or suitable modifications thereof known to those skilled in the art. The assay can be used to eliminate agents which specifically affect binding to hH1 receptors.

EXAMPLE 11
Exemplary Counter Screens
1. Assay Title: Dopamine D2, D3, D4 in vitro Screen
Objective of the Assay The objective of this assay is to eliminate agents which specifically affect binding of [3H] spiperone to cells expressing human dopamine receptors D2, D3 or D4.
Method Modified from VanTol et al., *Nature* (1991), 350: 610–613.

Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCI pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1*a*
Objective of the Assay

The objective of this assay is to eliminate agents which specifically affect binding to cloned human 5HT1a receptor.
Method Modified from Schelegel and Peroutka, Biochemical Pharmacology (1986), 35: 1943–1949.

Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-di propylamino- 1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters.

EXAMPLE 12
Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra

Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/ 95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ values are calculated for each group using GraphPad Inplot software. $pA_2$ (–log $K_b$) values were obtained from Schild plot when three or more concentrations were tested. When less than three concentrations of antagonist are tested, $K_b$ values are calculated according to the following formula $$K_b = \frac{[B]}{x-1},$$

where x is the ratio of $EC_{50}$ of agonist in the presence and absence of antagonist and [B] is the antagonist concentration.

2. Measurement of Intra-Urethral Pressure in Anesthetized Dogs

PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of formula:

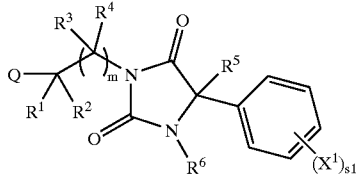

wherein Q is

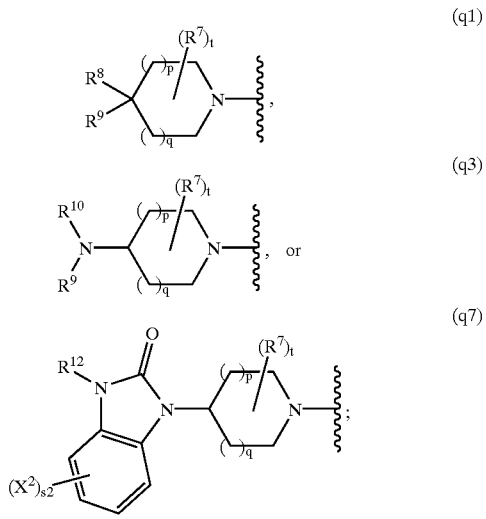

$R^1$, $R^2$, $R^3$ and $R^4$ are each independently selected from hydrogen, fluorine, $C_1$–$C_6$ alkyl, and $C_3$–$C_8$ cycloalkyl;

$R^5$ is $C_1$–$C_6$ alkyl, phenyl, substituted phenyl, naphthyl, substituted naphthyl, heterocyclic, or substituted heterocyclic; wherein each of the substituents on substituted phenyl or substituted naphthyl is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $C_2$–$C_8$ alkoxyalkyl, or fluorinated $C_2$–$C_8$ alkoxyalkyl; and wherein each of the substituents on substituted heterocyclic is independently halogen, cyano, $C_1$–$C_6$ alkyl, fluorinated $C_1$–$C_6$ alkyl, $C_1$–$C_6$ alkoxy, fluorinated $C_1$–$C_6$ alkoxy, $(CH_2)_{0-4}CO_2R^d$, $(CH_2)_{0-4}C(=O)N(R^d)_2$, $C_2$–$C_8$ alkoxyalkyl, fluorinated $C_2$–$C_8$ alkoxyalkyl, or phenyl;

$R^6$ is hydrogen, $C_1$–$C_6$ alkyl, fluorinated $C_1$–$C_6$ alkyl, $C_3$–$C_8$ cycloalkyl, fluorinated $C_3$–$C_8$ cycloalkyl, $(CH_2)_{1-4}CO_2R^d$, $(CH_2)_{1-4}C(=O)N(R^d)_2$, $C_2$–$C_8$ alkoxyalkyl, or fluorinated $C_2$–$C_8$ alkoxyalkyl;

each $R^7$ is a substituent connected to a ring atom other than $C(R^8R^9)$, spiro substituted carbon, or N and is independently hydrogen, $C_1$–$C_4$ alkyl, or $(CH_2)_{0-2}CO_2R^d$;

$R^8$ is cyano, $CO_2R^d$, $CON(R^d)_2$, aryl, or substituted aryl; wherein each of the substituents on substituted aryl is independently halogen, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$alkoxy, fluorinated $C_1$–$C_6$ alkoxy, $(CH_2)_{0-4}CO_2R^d$, $(CH_2)_{0-4}SO_2R^d$, $(CH_2)_{0-4}C(=O)N(R^d)_2$, $C_2$–$C_8$ alkoxyalkyl, or fluorinated $C_2$–$C_8$ alkoxyalkyl;

$R^9$ is aryl, substituted aryl, heteroaryl, or substituted heteroaryl; wherein each of the substituents on substituted aryl is independently halo, cyano, hydroxy, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $(CH_2)_{0-4}$ $C(=O)N(R^d)_2$, $(CH_2)_{0-4}SO_2R^d$, $C_2$–$C_8$ alkoxyalkyl, or fluorinated $C_2$–$C_8$ alkoxyalkyl; and wherein each of the substitutents on substituted heteroaryl is independently halogen, cyano, $N(R^d)_2$, $(CH_2)_{0-4}C(=O)N(R^d)_2$, $(CH_2)_{0-4}SO_2N(R^d)_2$, $(CH_2)_{0-4}SO_2R^d$, phenyl, $C_1$–$C_6$ alkyl, fluorinated $C_1$–$C_6$ alkyl, $C_3$–$C_8$ cycloalkyl, fluorinated $C_3$–$C_8$ cycloalkyl, $C_1$–$C_6$ alkoxy, fluorinated $C_1$–$C_6$ alkoxy, $(CH_2)_{0-4}CO_2R^d$, $C_2$–$C_8$ alkoxyalkyl, or fluorinated $C_2$–$C_8$ alkoxyalkyl;

$R^{10}$ is hydrogen, $C_1$–$C_6$ alkyl, or fluorinated $C_1$–$C_6$ alkyl;

$R^{12}$ is hydrogen, $C_1$–$C_4$ alkyl, or fluorinated $C_1$–$C_4$ alkyl;

each $X^1$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

D is absent, $[C(R^aR^b)]_{1-4}$, $O[C(R^aR^b)]_{1-2}$, $[C(R^aR^b)]_{1-2}O$, $C(R^a)=C(R^b)$, $C(R^aR^b)—C(R^a)=C(R^b)$, or $C(R^a)=C(R^b)—C(R^aR^b)$;

E is absent, $C(=O)$, $C(=O)O$, $N(SO_2R^c)C(R^aR^b)$, $N(R^c)C(=O)$, or $N(R^c)C(=O)O$, provided that (i) when E is absent, D is $[C(R^aR^b)]_{2-4}$, $O[C(R^aR^b)]_{1-2}$, $[C(R^aR^b)]_{1-2}O$, $C(R^a)=C(R^b)$, $C(R^aR^b)—C(R^a)=C(R^b)$, or $C(R^a)=C(R^b)—C(R^aR^b)$; (ii) when E is $C(=O)$ or $C(=O)O$, D is $C(R^aR^b)$ or $C(R^aR^b)C(R^aR^b)$; and (iii) when E is $N(SO_2R^c)C(R^aR^b)$, $N(R^c)C(=O)$ or $N(R^c)C(=O)O$, D is absent or $C(R^aR^b)$;

L is $[C(R^aR^b)]_{1-2}$;

M is $C(=O)$, $C(=O)O$, or $N(R^c)C(=O)$;

each $X^2$ is independently hydrogen, halogen, cyano, $C_1$–$C_6$ alkyl, $C_3$–$C_8$ cycloalkyl, fluorinated $C_1$–$C_6$ alkyl, fluorinated $C_3$–$C_8$ cycloalkyl, $(CH_2)_{0-4}CO_2R^d$, $(CH_2)_{0-4}C(=O)N(R^d)_2$, $C_1$–$C_6$ alkoxy, fluorinated $C_1$–$C_6$ alkoxy, $C_2$–$C_8$ alkoxyalkyl, or fluorinated $C_2$–$C_8$ alkoxyalkyl;

$R^a$, $R^b$, and $R^c$ are each independently hydrogen, $C_1$–$C_4$ alkyl, or fluorinated $C_1$–$C_4$ alkyl;

$R^d$ is hydrogen, $C_1$–$C_6$ alkyl, or fluorinated $C_1$–$C_6$ alkyl;

m is an integer from 1 to 4;

p and q are each independently integers from 0 to 3;

r is an integer equal to 0 or 1;

s1 is an integer from 0 to 5;

s2 is an integer from 0 to 4; and t is an integer from 0 to 4;

and provided that when Q is of formula (q7), then

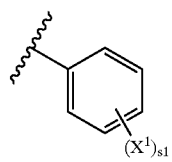

$(X^1)_{s1}$ is not phenyl, $R^5$ is substituted phenyl, and m is 2;
or a pharmaceutically acceptable salt thereof.

2. The compound according to claim 1, wherein
one of $R^1$ and $R^2$ is hydrogen and the other of $R^1$ and $R^2$ is hydrogen, $C_1$–$C_6$ alkyl, or $C_3$–$C_8$ cycloalkyl;

one of $R^3$ and $R^4$ is hydrogen and the other of $R^3$ and $R^4$ is hydrogen, $C_1$–$C_6$ alkyl, or $C_3$–$C_8$ cycloalkyl;

$R^5$ is $C_1$–$C_6$ alkyl, phenyl, napthyl, mono- or di- substituted phenyl or naphthyl, heterocyclic, or mono- or di-substituted heterocyclic; wherein heterocyclic is pyridyl, thienyl, or furanyl;

$R^6$ is hydrogen, $C_1$–$C_4$ alkyl, fluorinated $C_1$–$C_4$ alkyl, $C_3$–$C_6$ cycloalkyl, fluorinated $C_3$–C6 cycloalkyl, $(CH_2)_{1-2}CO_2R^d$, $(CH_2)_{1-2}C(=O)N(R^d)_2$, $C_2$–$C_8$ alkoxyalkyl; or fluorinated $C_2$–$C_8$ alkoxyalkyl;

each $R^7$ is independently hydrogen, $C_1$–$C_4$ alkyl, or $CO_2R^d$;

$R^8$ is cyano, $CO_2R^d$, $CON(R^d)_2$, phenyl, or mono- or di- or tri-substituted phenyl;

$R^9$ is phenyl, naphthyl, substituted phenyl, or substituted naphthyl; or pyridyl, pyrazinyl, thienyl, or furanyl; or substituted pyridyl, pyrazinyl, thienyl, or furanyl;

$R^d$ is hydrogen, $C_1$–$C_4$ alkyl, or $(CH_2)_{0-4}CF_3$;

m is an integer from 1 to 3;

p and q are each integers from 0 to 3, provided that the sum of m and n is an integer less than or equal to 3;

s1 is an integer from 0 to 3;

s2 is an integer from 0 to 2; and t is an integer from 0 to 2;

or a pharmaceutically acceptable salt thereof.

3. The compound according to claim 2, wherein Q is

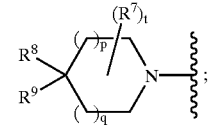

(q1)

or a pharmaceutically acceptable salt thereof.

4. The compound according to claim 3, having the formula

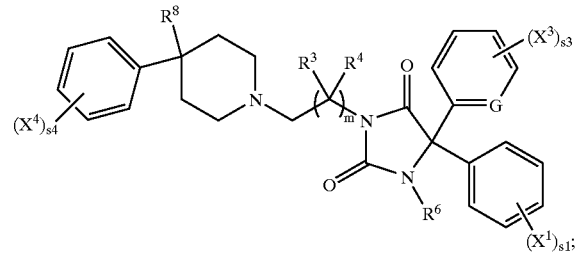

wherein
G is N or $CX^3$;

one of $R^3$ and $R^4$ is hydrogen and the other of $R^3$ and $R^4$ is hydrogen or $C_1$–$C_4$ alkyl;

$R^6$ is hydrogen, methyl, ethyl, $CH_2OCH_3$, $CH_2OCH_2CH_3$, $CH_2CO_2CH_3$, or $CH_2CO_2CH_2CH_3$;

$R^8$ is cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}OCF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^d$ is hydrogen, methyl, ethyl, or $CF_3$;

m is an integer equal to 2 or 3;

s3 is an integer from 0 to 3; and s4 is an integer from 0 to 2;

or a pharmaceutically acceptable salt thereof.

5. The compound according to claim 4, wherein the compound is selected from the group consisting of (+/−)-3-[2-methyl-3-(4-phenyl-4-cyanopiperidin-1-yl) propyl]-5,5-bis(4-methylphenyl)-imidazolin-2,4-dione;

(+/−)-3-{3-[4-(2-methylphenyl)-4-cyanopiperidin-1-yl] propyl}-5-(4-methylphenyl)-5-(2-pyridyl)-imidazolin-2, 4-dione;

and pharmaceutically acceptable salts thereof.

6. The compound according to claim 3, having the formula

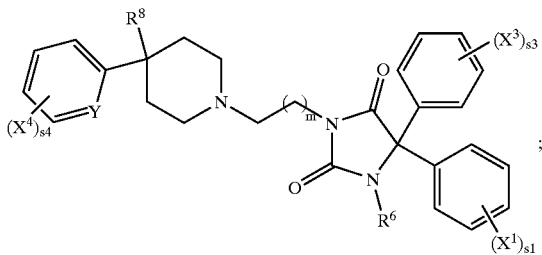

wherein

Y is N or $CX^4$;

$R^6$ is hydrogen, methyl, ethyl, $CH_2OCH_3$, $CH_2OCH_2CH_3$, $CH_2CO_2CH_3$, or $CH_2CO_2CH_2CH_3$;

$R^8$ is cyano, $CO_2R^d$, $CON(R^d)_2$, phenyl, or mono- or di-substituted phenyl; wherein each of the substituents on substituted phenyl is independently halogen, cyano, hydroxy, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$; or $(CH_2)_{1-4}OCF_3$;

each $X^1$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^3$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

$R^d$ is hydrogen, methyl, ethyl, or $CF_3$;

m is an interger equal to 2 or 3;

s3 is an integer from 0 to 3; and s4 is an integer from 0 to 2;

or a pharmaceutically acceptable salt thereof.

7. The compound according to claim 6, having the formula

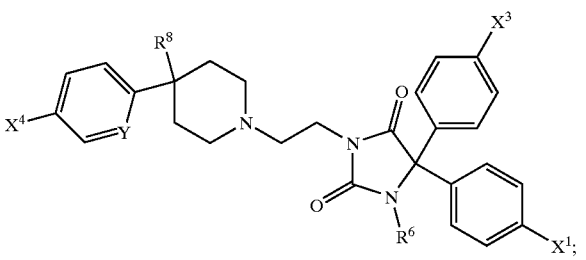

wherein $R^6$ is hydrogen, methyl, $CH_2OCH_3$, or $CH_2CO_2CH_2CH_3$;

$R^8$ is cyano;

$X^1$ is hydrogen, fluorine, chlorine, cyano, methyl, ethyl, methoxy, ethoxy, $CF_3$, or $OCF_3$;

$X^3$ is hydrogen, fluorine, chlorine, cyano, methyl, ethyl, methoxy, ethoxy, $CF_3$, or $OCF_3$; and each $X^4$ is independently hydrogen, fluorine, chlorine, cyano, methyl, ethyl, methoxy, ethoxy, $CF_3$, or $OCF_3$;

or a pharmaceutically acceptable salt thereof.

8. The compound according to claim 7, wherein the compound is selected from the group consisting of 3-[3-(4-phenyl-4-cyanopiperidin-1-yl)propyl]-5,5-bis(4-methylphenyl)-imidazolin-2,4-dione;

3-{3-[4-phenyl-4-cyanopiperidin-1-yl]propyl}-5,5-bis(4-chlorophenyl)-imidazolin-2,4-dione;

(+/−)-3-{3-[4-phenyl-4-cyanopiperidin-1-yl]propyl}-5-(4-methylphenyl)-5-phenyl-imidazolin-2,4-dione;

3-{3-[4-(2-methylphenyl)-4-cyanopiperidin-1-yl]propyl}-5,5-bis(4-methylphenyl)-imidazolin-2,4-dione;

3-{3-[4-(2-methylphenyl)-4-cyanopiperidin-1-yl]propyl}-5,5-bis(4-fluorophenyl)-imidazolin-2,4-dione;

3-{3-[4-(2-pyridyl)piperidin-1-yl]propyl}-5,5-bis(4-methylphenyl)-imidazolin-2,4-dione;

3-[3-(4-phenyl-4-cyanopiperidin-1-yl)propyl]-5,5-bis(phenyl)-imidazolin-2,4-dione;

(3-{3-[4-(4-fluoro-2-cyanophenyl)piperidin-1-yl]propyl}-5,5-bis(4-methylphenyl)-imidazolin-2,4-dione;

1-methyl-3-{3-[4-(2-methylphenyl)-4-cyanopiperidin-1-yl]propyl}-bis-5,5-(4-methylphenyl)-imidazolin-2,4-dione;

1-ethoxycarbonylmethyl-3-{3-[4-(2-methylphenyl)-4-cyanopiperidin-1-yl]propyl}-bis-5,5-(4-methylphenyl)-imidazolin-2,4-dione;

1-methoxymethyl-3-{3-[4-(2-methylphenyl)-4-cyanopiperidin-1-yl]propyl)}-5,5-bis(4-methylphenyl)-imidazolin-2,4-dione;

and pharmaceutically acceptable salts thereof.

9. The compound according to claim 3, wherein Q is a group of formula (q1);

$R^5$ is $C_1$–$C_6$ alkyl;

$R^8$ is cyano, $CO_2R^d$, $CON(R^d)_2$, phenyl, or mono- or di- or tri-substituted phenyl; and m is an integer equal to 2 or 3;

or a pharmaceutically acceptable salt.

10. The compound according to claim 9, wherein the compound is selected from the group consisting of (+/−)-3-{3-[4-phenyl-4-cyanopiperidin-1-yl]propyl}-5-methyl-5-phenyl-imidazolin-2,4-dione;

(+/−)-3-{3-[4-(2-methylphenyl)-4-cyanopiperidin-1-yl]-propyl}-5-isopropyl-5-(4-methylphenyl)-imidazolin-2,4-dione;

(+/−)-3-{3-[4-(2-methylphenyl)-4-cyanopiperidin-1-yl] propyl}-5-pentyl-5-(4-methylphenyl)-imidazolin-2,4-dione;

(+/−)-3-{3-[4-(2-methylphenyl)-4-cyanopiperidin-1-yl] propyl}-5-pentyl-5-(3,4-difluoro-phenyl)-imidazolin-2,4-dione;

(+/−)-3-{3-[4-(2-methylphenyl)-4-cyanopiperidin-1-yl] propyl}-5-pentyl-5-(4-chlorophenyl)-imidazolin-2,4-dione;

and pharmaceutically acceptable salts thereof.

11. The compound according to claim 2, wherein the compound is of formula:

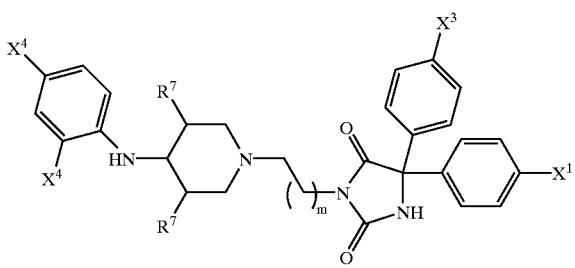

wherein $X^1$ is hydrogen, fluorine, chlorine, cyano, methyl, ethyl, $CF_3$, methoxy, ethoxy, $OCF_3$, or $OCH_2CF_3$;

$X^3$ is hydrogen, fluorine, chlorine, cyano, methyl, ethyl, $CF_3$, methoxy, ethoxy, $OCF_3$, or $OCH_2CF_3$;

each $X^4$ is independently hydrogen, halogen, cyano, $C_1$–$C_4$ alkyl, $(CH_2)_{0-4}CF_3$, $C_1$–$C_4$ alkoxy, $OCF_3$, $(CH_2)_{0-4}CO_2R^d$, $(CH_2)_{1-4}OCH_3$, or $(CH_2)_{1-4}OCF_3$;

each $R^7$ is independently hydrogen, methyl, ethyl, $CO_2CH_3$, or $CO_2CH_2CH_3$; and m is an integer equal to 2 or 3;

or a pharmaceutically acceptable salt thereof.

12. The compound according to claim 11, wherein the compound is (+/−)-3-{3-[4-(cis-2-chlorophenylamino-3-methoxycarbonylpiperidin-1-yl]propyl}-5,5-bis(4-methylphenyl)-imidazolin-2,4-dione;

or a pharmaceutically acceptable salt thereof.

13. The compound according to claim 2, wherein the compound is of formula:

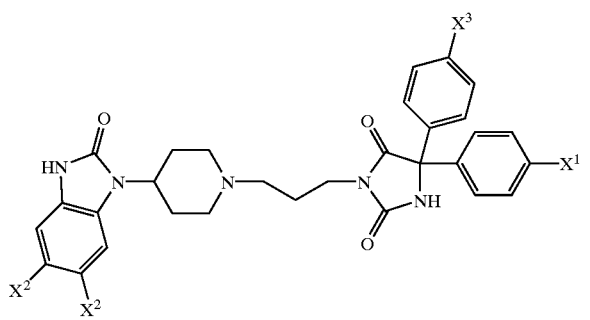

wherein $X^1$ is fluorine, chlorine, cyano, methyl, ethyl, $CF_3$, methoxy, ethoxy, $OCF_3$, or $OCH_2CF_3$;

each $X^2$ is independently hydrogen, fluorine, chlorine, cyano, methyl, ethyl, $CF_3$, methoxy, ethoxy, $OCF_3$, $CH_2CO_2CH_3$, $CH_2OCH_3$, or $CH_2OCF_3$; and $X^3$ is fluorine, chlorine, cyano, methyl, ethyl, $CF_3$, methoxy, ethoxy, $OCF_3$, or $OCH_2CF_3$;

or a pharmaceutically acceptable salt thereof.

14. The compound according to claim 13, wherein the compound is

3-{3[4-(5-chloro-2-oxo-1-benzimidazolinyl)piperidin-1-yl]propyl}-5,5-bis(4-methylphenyl)-imidazolin-2,4-dione;

or a pharmaceutically acceptable salt thereof.

15. A pharmaceutical composition comprising a therapeutically effective amount of the compound according to claim 1 and a pharmaceutically acceptable carrier.

16. A pharmaceutical composition made by combining a therapeutically effective amount of the compound according to claim 1 and a pharmaceutically acceptable carrier.

17. A process for making a pharmaceutical composition comprising combining a therapeutically effective amount of the compound according to claim 1 and a pharmaceutically acceptable carrier.

18. The composition according to claim 15 further comprising a therapeutically effective amount of a testosterone 5-alpha reductase inhibitor.

19. The composition according to claim 18, wherein the testosterone 5-alpha reductase inhibitor is a type 1, a type 2, both a type 1 and a type 2, or a dual type 1 and type 2 testosterone 5-alpha reductase inhibitor.

20. The composition according to claim 19, wherein the testosterone 5-alpha reductase inhibitor is a type 2 testosterone 5-alpha reductase inhibitor.

21. The composition according to claim 20, wherein the testosterone 5-alpha reductase inhibitor is finasteride.

22. A method of treating benign prostatic hyperplasia in a subject in need thereof which comprises administering to the subject a therapeutically effective amount of the compound according to claim 1.

23. The method according to claim 22, wherein the compound does not cause a fall in blood pressure at dosages effective to alleviate benign prostatic hyperlasia.

24. The method according to claim 22, wherein the compound is administered in combination with a therapeutically effective amount of a testosterone 5-alpha reductase inhibitor.

25. The method according to claim 24, wherein the testosterone 5-alpha reductase inhibitor is finasteride.

26. A method of treating benign prostatic hyperplasia in a subject in need thereof which comprises administering a therapeutically effective amount of the composition according to claim 15.

27. The method according to claim 26, wherein the composition further comprises a therapeutically effective amount of a testosterone 5-alpha reductase inhibitor.

28. A method of relaxing lower urinary tract tissue in a subject in need thereof which comprises administering to the subject a therapeutically effective amount of the compound according to claim 1.

29. The method according to claim 28, wherein the compound is administered in combination with a testosterone 5-alpha reductase inhibitor.

30. The method according to claim 29, wherein the testosterone 5-alpha reductase inhibitor is finasteride.

31. A method of eliciting an alpha 1a antagonizing effect in a mammal in need thereof, comprising administering to the mammal a therapeutically effective amount of the compound according to claim 1.

* * * * *